United States Patent
Jeong et al.

(10) Patent No.: US 9,861,333 B2
(45) Date of Patent: Jan. 9, 2018

(54) X-RAY IMAGING APPARATUS AND CONTROL METHOD FOR THE SAME

(71) Applicants: SAMSUNG ELECTRONICS CO., LTD., Suwon-si (KR); KOREA ADVANCED INSTITUTE OF SCIENCE AND TECHNOLOGY, Daejeon-si (KR)

(72) Inventors: Kye Young Jeong, Suwon-si (KR); Jae Hak Lee, Yongin-si (KR); Young Hun Sung, Hwaseong-si (KR); Jong Chul Ye, Daejeon (KR); Min Ji Lee, Daejeon (KR); Yo Seob Han, Bucheon-si (KR)

(73) Assignees: SAMSUNG ELECTRONICS CO., LTD., Suwon-si (KR); KOREA ADVANCED INSTITUTE OF SCIENCE AND TECHNOLOGY, Daejeon-si (KR)

( * ) Notice: Subject to any disclaimer, the term of this patent is extended or adjusted under 35 U.S.C. 154(b) by 24 days.

(21) Appl. No.: 14/744,269

(22) Filed: Jun. 19, 2015

(65) Prior Publication Data
US 2015/0366528 A1 Dec. 24, 2015

(30) Foreign Application Priority Data

Jun. 20, 2014 (KR) .................. 10-2014-0075989
Mar. 23, 2015 (KR) .................. 10-2015-0040015

(51) Int. Cl.
*G06K 9/00* (2006.01)
*A61B 6/00* (2006.01)
(Continued)

(52) U.S. Cl.
CPC ............ *A61B 6/5258* (2013.01); *A61B 6/032* (2013.01); *A61B 6/5205* (2013.01); *G06T 11/005* (2013.01)

(58) Field of Classification Search
None
See application file for complete search history.

(56) References Cited

U.S. PATENT DOCUMENTS 5,594,767 A * 1/1997 Hsieh .................. G06T 5/004
378/8
2008/0232718 A1* 9/2008 Avinash .................. A61B 6/032
382/305
(Continued)

FOREIGN PATENT DOCUMENTS

JP 6-181918 A 7/1994
JP 2000-81318 A 3/2000
(Continued)

OTHER PUBLICATIONS

Communication dated Apr. 19, 2016 issued by Korean Intellectual Property Office in counterpart Korean Application No. 10-2015-0040015.
(Continued)

*Primary Examiner* — Atiba O Fitzpatrick
(74) *Attorney, Agent, or Firm* — Sughrue Mion, PLLLC

(57) ABSTRACT

An X-ray imaging apparatus includes a back projected image generator configured to generate a back projected image with respect to a projected image of a field of view (FOV), and an image restorer configured to obtain frequency components of the back projected image, generate restored images for frequencies based on the frequency components of the back projected image, and generate a restored image with respect to the back projected image by synthesizing the restored images for the frequencies.

17 Claims, 32 Drawing Sheets

(51) Int. Cl.
    *A61B 6/03* (2006.01)
    *G06T 11/00* (2006.01)

(56) References Cited

U.S. PATENT DOCUMENTS

2012/0308100 A1* 12/2012 Pack ................... G06T 11/006
                                                            382/131
2014/0119668 A1*  5/2014 Kwon .................. G06T 11/005
                                                            382/232

FOREIGN PATENT DOCUMENTS

JP    2011-139894 A     7/2011
KR    10-2012-0006926 A 1/2012

OTHER PUBLICATIONS

Communication dated Oct. 17, 2016, issued by the Korean Intellectual Property Office in counterpart Korean application No. 10-2015-0040015.
Communication dated Jan. 11, 2017 issued by Korean Intellectual Property Office in counterpart Korean Patent Application No. 10-2015-0040015.

* cited by examiner

X-RAY IMAGING APPARATUS AND CONTROL METHOD FOR THE SAME

CROSS-REFERENCE TO RELATED APPLICATIONS

This application claims priority to Korean Patent Application No. 10-2014-0075989, filed on Jun. 20, 2014 and No. 10-2015-0040015, filed on Mar. 23, 2015 in the Korean Intellectual Property Office, the disclosure of which is incorporated herein by reference in its entirety.

BACKGROUND

1. Field

Exemplary embodiments consistent with the present disclosure relate to an X-ray imaging apparatus and control method for the same.

2. Description of the Related Art

An X-ray imaging apparatus is an apparatus that can radiate X-rays to an object such as a human body or other types of objects and acquire an internal image of the object using the X-rays transmitted through the object. Transmissivity of the X-rays is different according to characteristics of a material of which the object is constituted, and therefore the internal structure of the object can be visualized by detecting the intensity or strength of the X-rays transmitted through the object. The internal structure of the object may be readily determined through the X-ray imaging apparatus, and therefore the X-ray imaging apparatus may be used in detecting disorders such as lesions of a human body in the medical field or in checking the inside of baggage in an airport.

Examples of such an X-ray imaging apparatus include a digital radiography (DR) apparatus, a computed tomography (CT) apparatus, a full field digital mammography (FFDM) apparatus, and the like.

The X-ray imaging apparatus may include an X-ray source that radiates X-rays and an X-ray detector that detects X-rays transmitted through an object, may perform arithmetic operations based on electrical signals output from the X-ray detector, and may generate a restored image close to an ideal image inside the object. In addition, the X-ray imaging apparatus may use the restored image or an image obtained by performing post-processing on the restored image as an X-ray image of the object to thereby display the X-ray image.

SUMMARY

Therefore, it is an aspect of the exemplary embodiments to provide an X-ray imaging apparatus that reduces constraints of a generation time of a restored image and of a field of view (FOV) for generating the restored image, and a control method for the same.

Additional aspects of the exemplary embodiments will be set forth in part in the description which follows and, in part, will be obvious from the description, or may be learned by practice of the exemplary embodiments.

In accordance with an aspect of an exemplary embodiment, there is provided an X-ray imaging apparatus including: a back projected image generator configured to generate a back projected image with respect to a projected image of a field of view (FOV); and an image restorer configured to obtain frequency components of the back projected image, generate restored images for frequencies based on the frequency components of the back projected image, and generate a restored image with respect to the back projected image by synthesizing the restored images for the frequencies.

The FOV may include an entire region of an object or only a partial region of the object.

The image restorer may be configured to acquire a first low frequency component of the back projected image, and generate a low frequency restored image based on the first low frequency component.

The image restorer may be configured to acquire the first low frequency component by applying at least one of low pass filtering (LPF) and down sampling to the back projected image.

The image restorer may be configured to generate the low frequency restored image by applying a regulation function and a repetitive restoration method to the first low frequency component.

The image restorer may be configured to generate the low frequency restored image by applying a projection onto convex set (POCS) to the first low frequency component.

The image restorer may be configured to acquire a high frequency component of the back projected image based on the low frequency restored image, and generate a high frequency restored image based on the high frequency component.

The image restorer may be configured to acquire a second low frequency component of the back projected image by performing a Hilbert transform on the low frequency restored image, and acquire the high frequency component using a difference between the back projected image and the second low frequency component.

The image restorer may be configured to generate the high frequency restored image using the following Equation:

$$f_H(x) = \frac{H^{-1}\{w(x) \cdot g_H(x)\}}{w(x)} = \frac{-H\{w(x) \cdot g_H\}}{w(x)},$$

where $f_H(x)$ denotes the high frequency restored image, $g_H(x)$ denotes the high frequency component, $w(x)$ denotes a window function corresponding to the second low frequency component, H denotes the Hilbert transform, and $H^{-1}$ denotes an inverse Hilbert transform.

The back projected image generator may be configured to generate the back projected image by applying a derivative back projection (DBP) method to the projected image.

The X-ray imaging apparatus may further include an image corrector configured to generate a corrected image by correcting noise that occurs in the restored image due to a frequency loss.

The image corrector may generate the corrected image in which a loss frequency region where the frequencies are lost is minimized using a plurality of restored images which are different from one other with respect to the loss frequency region.

The image corrector may generate the corrected image in which the loss frequency region is minimized by synthesizing a plurality of extracted regions obtained by filtering the plurality of restored images in a frequency domain in different directions.

The image corrector may determine a direction of the filtering according to a direction of the loss frequency region that is present in the restored image.

The image corrector may generate the corrected image using the following Equation:

$$f_a(x) = \mathcal{F}^{-1}((W1)\mathcal{F}(f_1(x)) + (W2)\mathcal{F}(f_2(x)))$$

wherein $f_a(x)$ denotes the corrected image, $f_1(x)$ denotes a first restored image, $f_2(x)$ denotes a second restored image in which the first restored image is orthogonal to the loss frequency region, W1 denotes a first weight function that filters the first restored image so that the loss frequency region is minimized, W2 denotes a second weight function that filters the second restored image in a direction orthogonal to the first weight function, F denotes a Fourier transform, and $F^{-1}$ denotes an inverse Fourier transform.

The image corrector may generate the corrected image using the following Equation:

$$fa(x) = \mathcal{F}^{-1}\left(\sum_{i=1}^{N} W_i \mathcal{F}(f_i(x))\right) \text{ where } \sum_{i=1}^{n} W_i = 1$$

wherein $f_a(x)$ denotes the corrected image, $f_i(x)$ denotes the restored images having different loss frequency regions, $W_i$ denotes a weight function for filtering the restored image, F denotes a Fourier transform, and $F^{-1}$ denotes an inverse Fourier transform.

The image restorer may generate the plurality of restored images based on the plurality of back projected images generated according to different pi lines.

The loss frequency region may be present on a virtual orbital surface on which an X-ray source is not actually rotated.

In accordance with another aspect of an exemplary embodiment, there is provided a control method for an X-ray imaging apparatus including: generating a back projected image with respect to a projected image of a field of view (FOV) and obtaining frequency components of the back projected image; generating restored images for frequencies based on the frequency components of the back projected image; and generating a restored image with respect to the projected image by synthesizing the restored images for the frequencies.

The FOV may include an entire region of an object or only a partial region of the object.

The generating of the restored images for the frequencies may include acquiring a first low frequency component of the back projected image and generating a low frequency restored image based on the first low frequency component.

The generating of the restored images for the frequencies may include acquiring the first low frequency component by applying at least one of low pass filtering (LPF) and down sampling to the back projected image.

The generating of the restored images for the frequencies may include generating the low frequency restored image by applying a regulation function and a repetitive restoration method to the first low frequency component.

The generating of the restored images for the frequencies may include generating the low frequency restored image by applying a projection onto convex set (POCS) to the first low frequency component.

The generating of the restored images for the frequencies may include acquiring a high frequency component of the back projected image based on the low frequency restored image, and generating a high frequency restored image based on the high frequency component.

The generating of the restored images for the frequencies may include acquiring a second low frequency component of the back projected image by performing a Hilbert transform on the low frequency restored image, and acquiring the high frequency component using a difference between the back projected image and the second low frequency component.

The generating of the restored images for the frequencies may include generating the high frequency restored image using the following Equation:

$$f_H(x) = \frac{H^{-1}\{w(x) \cdot g_H(x)\}}{w(x)} = \frac{-H\{w(x) \cdot g_H\}}{w(x)},$$

where $f_H(x)$ denotes the high frequency restored image, $g_H(x)$ denotes the high frequency component, $w(x)$ denotes a window function corresponding to the second low frequency component, H denotes the Hilbert transform, and $H^{-1}$ denotes an inverse Hilbert transform.

The generating of the back projected image may include generating the back projected image by applying a derivative back projection (DBP) method to the projected image.

The control method for the X-ray imaging apparatus may further include generating a corrected image by correcting noise that occurs in the restored image due to a frequency loss.

The generating of the corrected image may include generating the corrected image in which a loss frequency region where the frequencies are lost is minimized using a plurality of restored images which are different from one other with respect to the loss frequency region.

The generating of the corrected image may include generating the corrected image in which the loss frequency region is minimized by synthesizing a plurality of extracted regions obtained by filtering the plurality of restored images in a frequency domain in different directions.

A direction of the filtering may be determined according to a direction of the loss frequency region that is present in the restored image.

The generating of the corrected image may include generating the plurality of restored images based on a plurality of back projected images generated according to different pi lines.

BRIEF DESCRIPTION OF THE DRAWINGS

These and/or other aspects of the exemplary embodiments will become apparent and more readily appreciated from the following description of the exemplary embodiments, taken in conjunction with the accompanying drawings of which.

DETAILED DESCRIPTION

Figure 1:
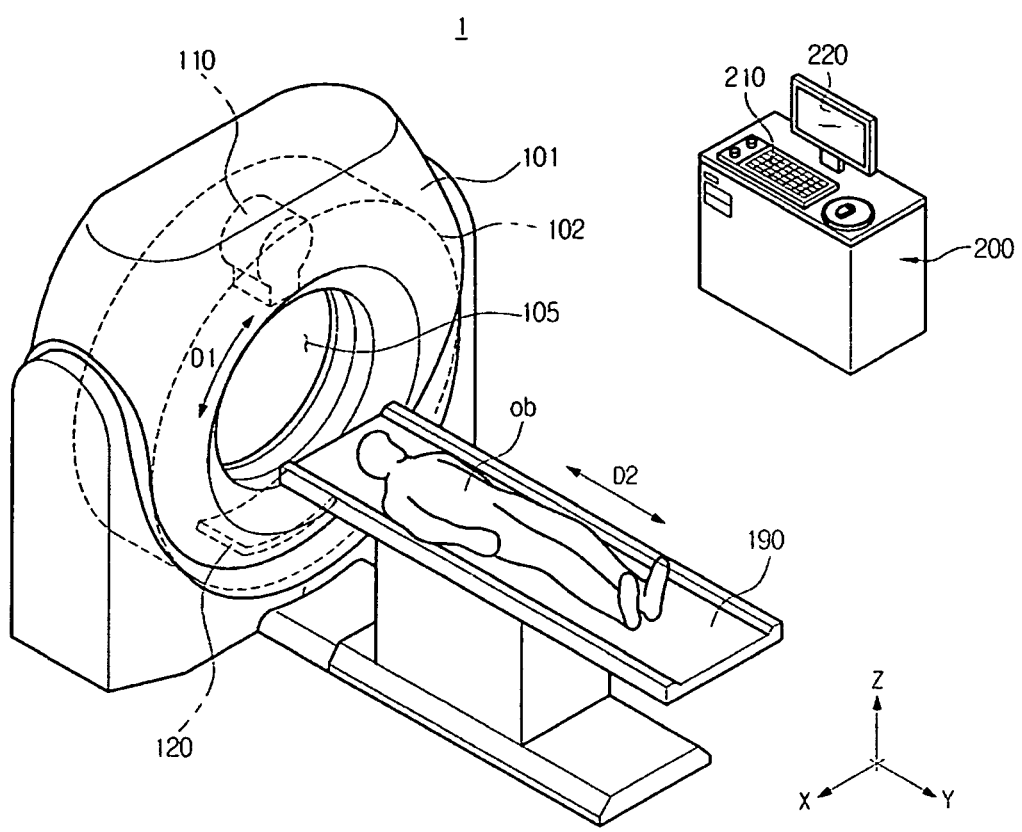
FIG. 1 is a perspective diagram showing an X-ray imaging apparatus in accordance with an exemplary embodiment.

Exemplary embodiments described in the present specification and configurations shown in the drawings are merely examples for the purpose of illustration only, and are not intended to limit the scope of the exemplary embodiments, and thus it should be understood that other equivalents and modifications could be made thereto without departing from the spirit and scope of the exemplary embodiments.

Hereinafter, an X-ray imaging apparatus and a control method for the X-ray imaging apparatus will be described in detail in accordance with exemplary embodiments which will be described with reference to the accompanying drawings. Like reference numerals refer to like elements throughout.

The structure or radiography method of the X-ray imaging apparatus may be changed depending on a radiographic part, the kind of an X-ray image, or the purpose of radiography. Specifically, types of X-ray imaging apparatuses include a general X-ray imaging apparatus that performs radiography on the chest, arms, legs, etc., an X-ray imaging apparatus using mammography, an X-ray imaging apparatus using fluoroscopy, an X-ray imaging apparatus using angiography, an X-ray imaging apparatus for cardiography, an X-ray imaging apparatus using tomography, and the like, and the X-ray imaging apparatus according to an exemplary embodiment may be one of the above-described X-ray imaging apparatuses or a combination of at least two thereof.

Hereinafter, for convenience of description, the X-ray imaging apparatus using tomography, particularly, an X-ray imaging apparatus that is implemented as a computed tomography (CT) apparatus, will be exemplarily described.

FIG. 1 is a perspective diagram showing an X-ray imaging apparatus in accordance with an exemplary embodiment.

As shown in FIG. 1, the X-ray imaging apparatus 1 may include a housing 101 for radiating and detecting X-rays, a table 190 for moving an object (ob), and a main body 200 for controlling operations of the X-ray imaging apparatus 1.

A cylindrical gantry 102 is mounted inside the housing 101. Inside the gantry 102, an X-ray source 110 that radiates X-rays and an X-ray detector 120 that detects X-rays are provided so as to face each other. The X-ray source 110 generates X-rays and irradiates the object (ob) with the generated X-rays, and includes a filtering unit that filters the radiated X-rays to be provided in the form of an X-ray source assembly. According to an exemplary embodiment, the object (ob) is not limited to any particular type of object, as long as the internal structure of the object (ob) can be visualized by the X-ray imaging apparatus 1. Thus, the object can be, for example, a human, an animal, an inanimate object, and the like.

The X-ray detector 120 may detect the X-rays transmitted through the object (ob), and may be provided on an opposite side of the X-ray source 110. The object (ob) may be positioned between the X-ray source 110 and the X-ray detector 120 according to the movement of the table 190, and the X-rays radiated from the X-ray source 110 may be transmitted through the object to be detected through the X-ray detector 120.

The gantry 102 may be rotated around a bore 105 at a constant angular velocity in accordance with a driving command, and therefore the X-ray source 110 and the X-ray detector 120 provided in the gantry 102 are also rotated while forming a predetermined axis. In this instance, the rotation direction of the gantry 102 may be defined as a direction D1. Detailed descriptions of the rotation of the gantry 102 will be made with reference to FIGS. 2 to 5 which will be described later.

The table 190 transports the object (ob) that is a target of X-ray radiography into the bore 105. The table 190 may be moved in a left and right direction (that is, X-axis direction), a front and back direction (that is, Y-axis direction), and a vertical (up and down) direction (that is, Z-axis direction) while remaining level with the ground. The table 190 may allow a region to be photographed, that is, may allow a field of view (FOV) to be positioned between the X-ray source 110 and the X-ray detector 120 while moving in the X-axis direction, the Y-axis direction, and the Z-axis direction. In this instance, a direction in which the table 190 is moved in the Y-axis may be defined as a direction D2. In addition, the FOV may be a whole region of the object (ob) or only a partial region thereof. The FOV may be a region of interest (ROI).

Figure 6:
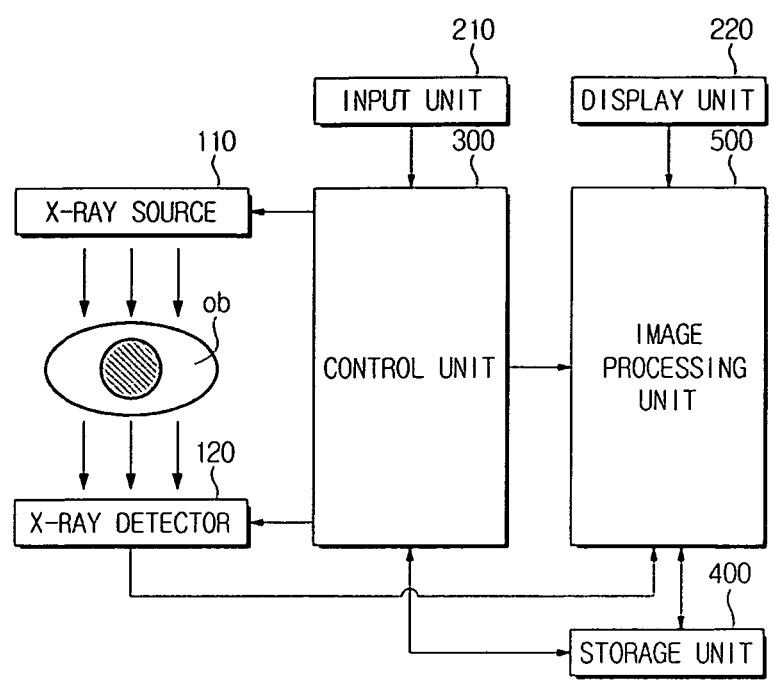
FIG. 6 is a control block diagram illustrating an X-ray imaging apparatus in accordance with an exemplary embodiment.

The main body 200 may house main components of the X-ray imaging apparatus 1, for example, a control unit (e.g., controller) (see 300 of FIG. 6). The control unit 300 may generate a variety of control signals for controlling rotation of the gantry 102, movement of the table 190, or the dose of X-rays radiated from the X-ray source 110, and this feature will be described later.

A user interface for user operation may be provided on an upper portion of the main body 200. The user interface may include an input unit 210 (e.g., inputter) that receives a user command for manipulating operations of the X-ray imaging apparatus 1, and a display unit 220 (e.g., display) that provides a screen or various types of screens related to the operations of the X-ray imaging apparatus 1. A user may be a person who performs diagnosis of an object using the X-ray imaging apparatus 1, that is, a medical staff including a doctor, a radiologist, a nurse, and the like, but is not limited thereto. The user is not limited to any particular type of user.

The input unit 210 may include a hardware input device such as various buttons and switches, a keyboard, a mouse, a track-ball, various levers, a handle, a stick, and the like for the purpose of the user's input. The input unit 210 may be provided on an upper portion of the main body 200 as shown in FIG. 1, or provided on a lower portion thereof when the input unit 210 is implemented by a foot switch, a foot pedal, and the like.

The input unit 210 may include a graphical user interface (GUI) such as a touch pad for the user's input, that is, a software input device. The touch pad may be implemented by a touch screen panel (TSP) to form a mutual layer structure with the display unit 220 which will be described later.

The user may input an X-ray radiography start command, a movement command of the table 190, and the like through the input unit 210, select the kind of radiography, or set the FOV. The user command input through the input unit 210 may be transmitted to the main body 200 through wired or wireless communication.

The display unit 220 may be provided as a cathode ray tube (CRT), a digital light processing (DLP) panel, a plasma display panel, a liquid crystal display (LCD) panel, an electroluminescence (EL) panel, an electrophoretic display (EPD) panel, an electrochromic display (ECD) panel, a light emitting diode (LED) panel, an organic light emitting diode (OLED) panel, or the like, but is not limited thereto.

As described above, when the display unit 220 is constituted of a TSP that forms the mutual layer structure with the touch pad, the display unit 220 may be used not only as a display device but also as an input device.

The display unit 220 may display a screen related to operation information of the X-ray imaging apparatus 1 such as a screen for selecting the kind of radiography, a screen for setting the FOV, or the like, and display X-ray images acquired by X-ray radiography. According to an exemplary embodiment, the X-ray image includes a restored image close to an ideal image inside of the object and an image obtained by performing post-processing on the restored image, and a detailed description of the restored image will be made later.

The X-ray image acquired by X-ray radiography may be a single cross-sectional image, a plurality of cross-sectional images, or a three-dimensional (3D) image or a 3D stereo image generated based on the plurality of cross-sectional images in accordance with the kind of X-ray radiography. In this instance, the 3D image refers to an image obtained by performing volume rendering on 3D volume data generated based on the plurality of cross-sectional images on the basis of a predetermined point of sight. That is, the 3D image denotes a 2D projected image obtained by projecting volume data to a 2D plane on the basis of a predetermined point of sight. The 3D stereo image refers to an image obtained in such a manner that left and right images are obtained by performing volume rendering on volume data at two points of sight corresponding to left and right eyes of a human body and the two obtained images are combined.

The display unit 220 shown in FIG. 1 may include a plurality of display devices, and may display different kinds of screens. As an example, the display unit 220 may include a first display device and a second display device. According to an exemplary embodiment, a single cross-sectional image may be displayed on the first display device, and a 3D image or a 3D stereo image may be displayed on the second display device. As another example, a screen related to operation information of the X-ray imaging apparatus 1 may be displayed on the first display device, and X-ray images acquired by X-ray radiography may be displayed on the second display device.

Figure 2:
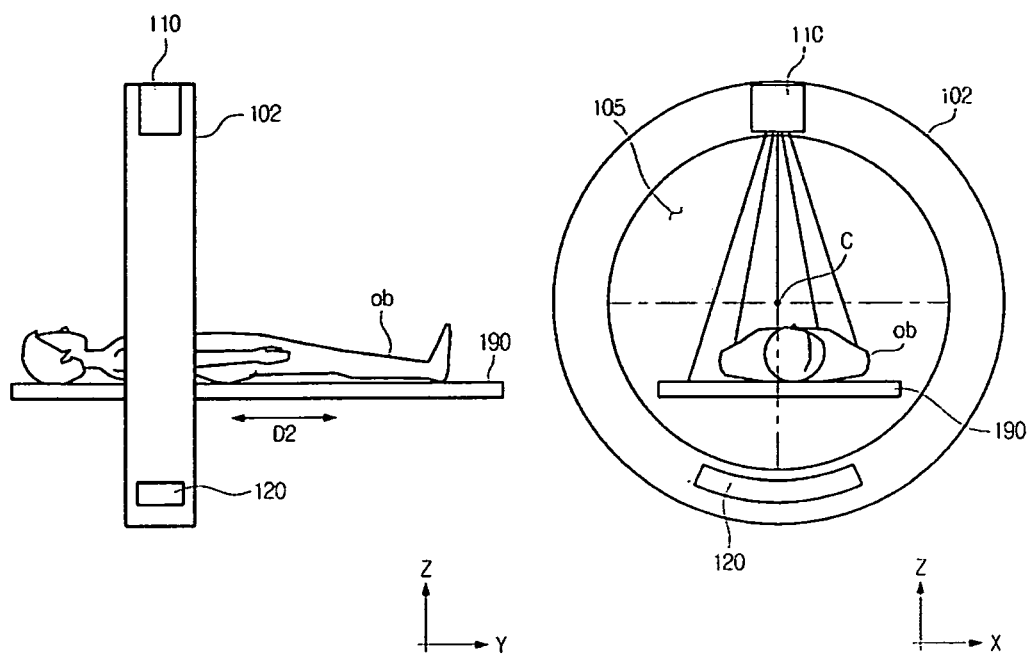
FIGS. 2 and 3 are diagrams for describing a movement of a table.
Figure 3:
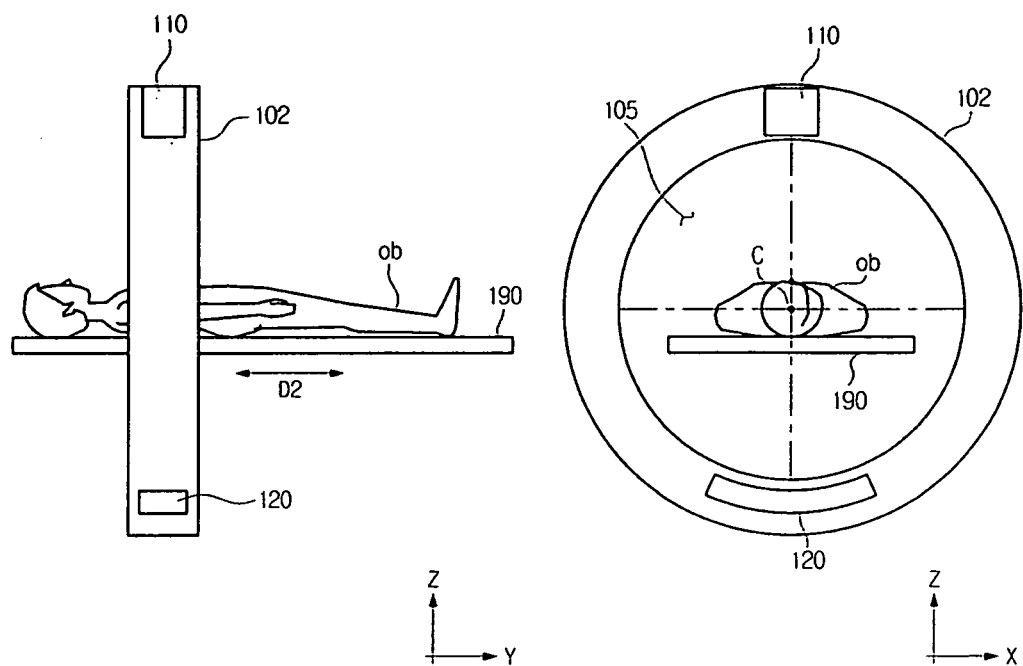
Figure 4:
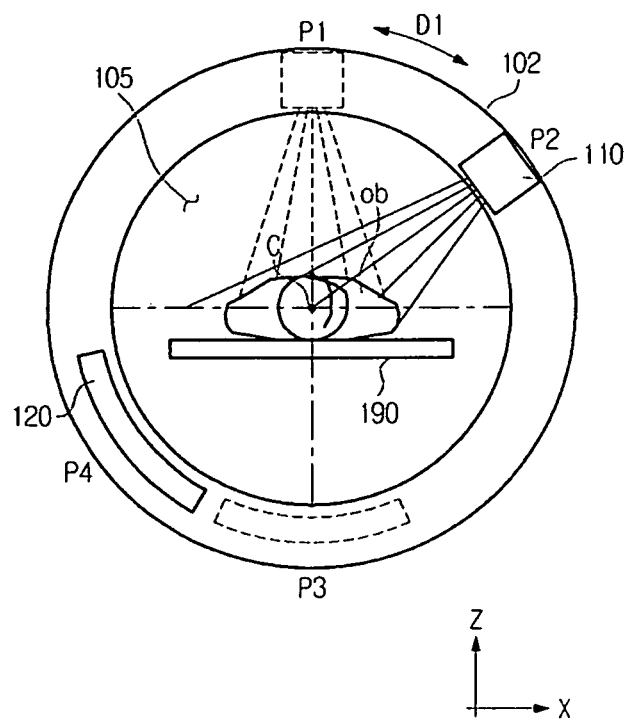
FIGS. 4 and 5 are diagrams for describing a rotation of a gantry.
Figure 5:
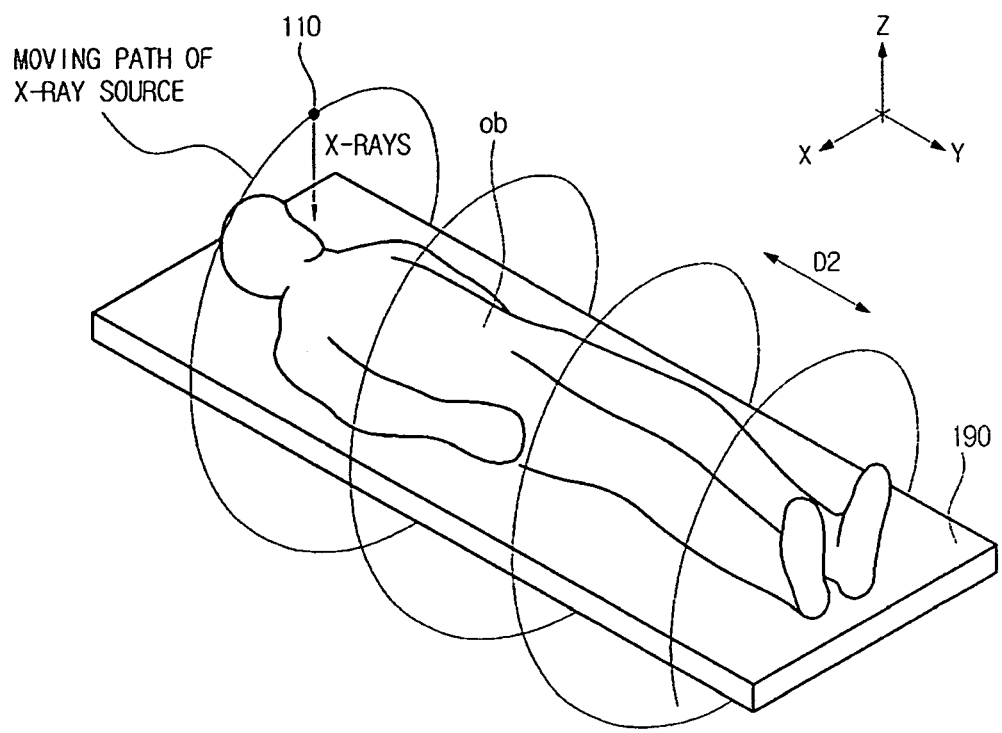

FIGS. 2 and 3 are diagrams for describing movement of a table, and FIGS. 4 and 5 are diagrams for describing rotation of a gantry.

Referring to FIGS. 2 and 3, the table 190 of the X-ray imaging apparatus 1 transports the object (ob) into the bore 105 to allow the set FOV to be positioned between the X-ray source 110 and the X-ray detector 120 while moving in the direction D2 in accordance with a driving command. The horizontal position or vertical height of the table 190 may be adjusted and then the table 190 may be moved into the bore 105, or the table 190 may be moved into the bore 105 and then the horizontal position or vertical height of the table 190 may be adjusted.

When the center of the object (ob) deviates from the center (C) of the bore 105, the table 190 is moved vertically or horizontally by a distance from the center (C) to align the center of the object (ob) with the center (C) of the bore 105. Thus, the X-ray imaging apparatus 1 may acquire a clearer X-ray image.

As shown in FIG. 4, the gantry 102 may start rotation in the direction D1 when X-ray radiography starts. The gantry 102 is rotated in accordance with a rotation rate and rotation speed which are input by a user or determined in advance, and the X-ray source 110 radiates X-rays to the object (ob) at a predetermined period or time interval. The X-ray detector 120 detects the X-rays transmitted through the object (ob) while rotating together with the X-ray source 110. For example, the X-ray source 110 rotates 360° using a position P1 as a starting position, passes through a position P2, and returns to the position P1, and radiates X-rays multiple times while rotating. The X-ray detector 120 rotates 360° using a position P3 as a starting position to correspond to the position of the X-ray source 110, passes through a position P4, and returns to the position P3. While returning to the position P3, the X-ray detector 120 detects transmitted X-rays corresponding to each instance of radiation of X-rays.

While the gantry 102 is rotated in the direction D1, the table 190 is moved in the direction D2 at a predetermined speed, so that the FOV completely passes through the inside of the bore 105, that is, between the X-ray source 110 and the X-ray detector 120. Thus, the moving path of the X-ray source 110 forms a spiral with respect to the FOV. For example, when the FOV is a whole region of the object (ob), the X-ray source 110 radiates X-rays while moving along a spiral path with respect to the object (ob), as shown in FIG. 5. The X-ray detector 120 is also moved while forming the spiral path with respect to the object (ob) in such a manner as to be symmetrically with the X-ray source 110.

The appearance of the X-ray imaging apparatus 1 has been described above, and components of the X-ray imaging apparatus 1 that generate a restored image and an X-ray image and operations of the components thereof will be hereinafter described with reference to FIG. 6.

FIG. 6 is a control block diagram illustrating an X-ray imaging apparatus in accordance with an exemplary embodiment.

Referring to FIG. 6, the X-ray imaging apparatus 1 includes the input unit 210 (e.g., inputter), the X-ray source 110, the X-ray detector 120, the control unit 300 (e.g., controller), a storage unit 400 (e.g., storage), an image processing unit 500 (e.g., image processor), and the display unit 220 (e.g., display).

Figure 7:
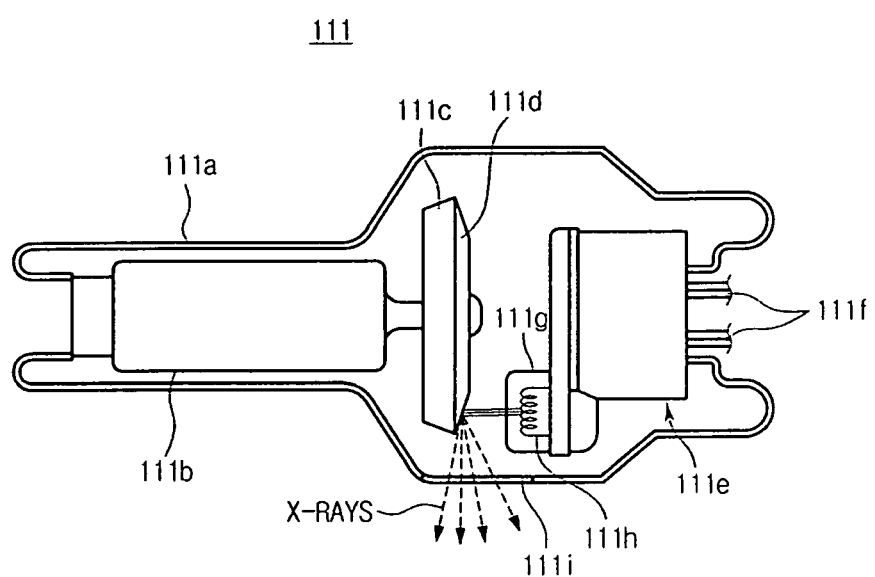
FIG. 7 is a cross-sectional diagram illustrating an internal structure of an X-ray tube.

The X-ray source 110 is a device that generates X-rays to radiate the generated X-rays to an object (ob), and may include an X-ray tube 111 as shown in FIG. 7 in order to generate X-rays. FIG. 7 is a cross-sectional diagram illustrating an internal structure of an X-ray tube.

The X-ray tube 111 may be implemented as a diode vacuum tube including an anode 111c and a cathode 111e, and the tubular body may be a glass tube 111a made of a rigid silicate glass or the like.

The cathode 111e includes a focusing electrode 111g that focuses filaments 111h and electrons, and the focusing electrode 111g may be referred to as a focusing cup. Thermoelectrons are generated in such a manner that the inside of the glass tube 111a is in a high vacuum state of approximately 10 mmHg and the filaments 111h of the cathode are heated to a high temperature. As an example of the filaments 111h, tungsten filaments may be used, and the filaments 111h may be heated by applying a current to an electric lead wire 111f connected to the filaments 111h. However, the exemplary embodiments are not limited to adopting the filaments 111h in the cathode 111e, and other configurations may also be implemented in accordance with other exemplary embodiments, for example, a carbon nanotube that can be driven by a high-speed pulse may be used as the cathode 111e.

The anode 111c may be mainly made of copper, and a target material 111d may be coated or disposed on a side of the anode 111c that faces the cathode 111e. As the target material, high-resistance materials such as Cr, Fe, Co, Ni, W, Mo, and the like may be used. A focal spot size is reduced along with an increase in the melting point of the target material.

When a high voltage is applied between the cathode 111e and the anode 111c, the thermoelectrons are accelerated and collide with the target material 111d of the anode to generate X-rays. The generated X-rays are radiated to the outside through a window 111i, and a beryllium (Be) thin film may be used as a material of the window.

The target material 111d may be rotated by a rotor 111b, and when the target material 111d is rotated, a heat accumulation rate may be increased 10 times or more per unit area compared to a case in which the target material 111d is fixed, and the focal spot size may be reduced.

The voltage applied between the cathode 111e and the anode 111c of the X-ray tube 111 is referred to as a tube voltage, and the magnitude of the tube voltage may be represented as a crest value kvp. When the tube voltage is increased, the speed of the thermoelectrons is increased and the thermoelectrons collide with the target material to generate X-rays, and therefore energy (energy of photons) of the generated X-rays is increased. A current flowing in the X-ray tube 111 may be referred to as a tube current, and represented as a mean value mA. When the tube current is increased, the dose of the X-rays (the number of photons of X-rays) is increased. That is, the energy of the X-rays may be controlled by the tube voltage, and the dose of the X-rays may be controlled by the tube current and an X-ray exposure time.

The X-ray source 110 may radiate X-rays to the whole region of the object (ob) or only a partial region inside the object (ob) according to the set FOV. In other words, when the whole region of the object (ob) is set as the FOV, the X-ray source 110 may radiate X-rays to the whole region of the object (ob), whereas when only the partial region inside the object (ob) is set as the FOV, the X-ray source 110 may radiate X-rays only to the corresponding region, thereby reducing an exposure level of X-rays.

The X-ray detector 120 is a device for detecting X-rays which are radiated from the X-ray source 110 and transmitted through the object (ob) or are directly transferred without being transmitted through the object (ob). The X-ray detector 120 may convert the detected X-rays into electrical signals, and in this instance, the converted electrical signals may be referred to as X-ray signals. The X-ray signals acquired by the X-ray detector 120 are transferred to the storage unit 400 or the image processing unit 500.

The X-ray detector 120 may be classified in accordance with a material of which the X-ray detector 120 is constituted, a method of converting the detected X-rays into electrical signals, or a method of acquiring electrical signals.

First, the X-ray detector 120 is classified as being constituted of a single element or constituted of a mixed element in accordance with the material of which it is constituted.

A case in which the X-ray detector 120 is constituted of the single element corresponds to a case in which a portion that detects X-rays to generate electrical signals and a portion that reads and processes electrical signals are constituted of a semiconductor composed of a single material or manufactured in a single process, and for example, corresponds to a case in which a single light-receiving element such as a charge coupled device (CCD) or a complementary metal oxide semiconductor (CMOS) is used.

A case in which the X-ray detector 120 is constituted of the mixed element corresponds to a case in which the portion that detects X-rays to generate electrical signals and the portion that reads and processes electrical signals are constituted of different materials or manufactured in different processes. For example, there are cases in which the X-rays are detected using a light-receiving element such as a photodiode, a CCD, or CdZnTe and the electrical signals are read and processed using a CMOS read out integrated circuit (ROIC), cases in which the X-rays are detected using a strip detector and the electrical signals are read and processed using the CMOS ROIC, cases in which an a-Si or a-Se flat panel system is used, and the like.

In addition, the method in which the X-ray detector 120 converts the X-rays into electrical signals is classified as a direct conversion method or an indirect conversion method.

In the direct conversion method, when X-rays are radiated, electron-hole pairs are temporarily generated inside a light-receiving element, and the electrons move to the anode and the holes move to the cathode due to the electric field applied to both ends of the light-receiving element. According to an exemplary embodiment, the X-ray detector 120 converts such movement into electrical signals. In the direct conversion method, a-Se, CdZnTe, HgI$_2$, PbI$_2$, or the like may be used as a material of the light-receiving element.

In the indirect conversion method, when X-rays radiated from the X-ray source 110 react with a scintillator to emit photons having wavelengths of the visible light region, the light-receiving element detects the emitted photons and converts the detected photons into electrical signals. In the indirect conversion method, a-Si or the like may be used as the light-receiving element, and a thin-film GADOX scintillator, a CSI (T1) having a micro columnar or needle structure, or the like may be used as the scintillator.

In addition, the method in which the X-ray detector 120 acquires electrical signals is classified as a charge integration mode of storing charges for a certain time and then acquiring signals from the stored charges, or a photon counting mode of performing counting every time when signals are generated by a single X-ray photon.

Any method among the above-described methods may be applied to the X-ray detector 120. In addition, the X-ray detector 120 may have a 2D array structure including a plurality of pixels 150 as shown in FIG. 8.

Figure 8:
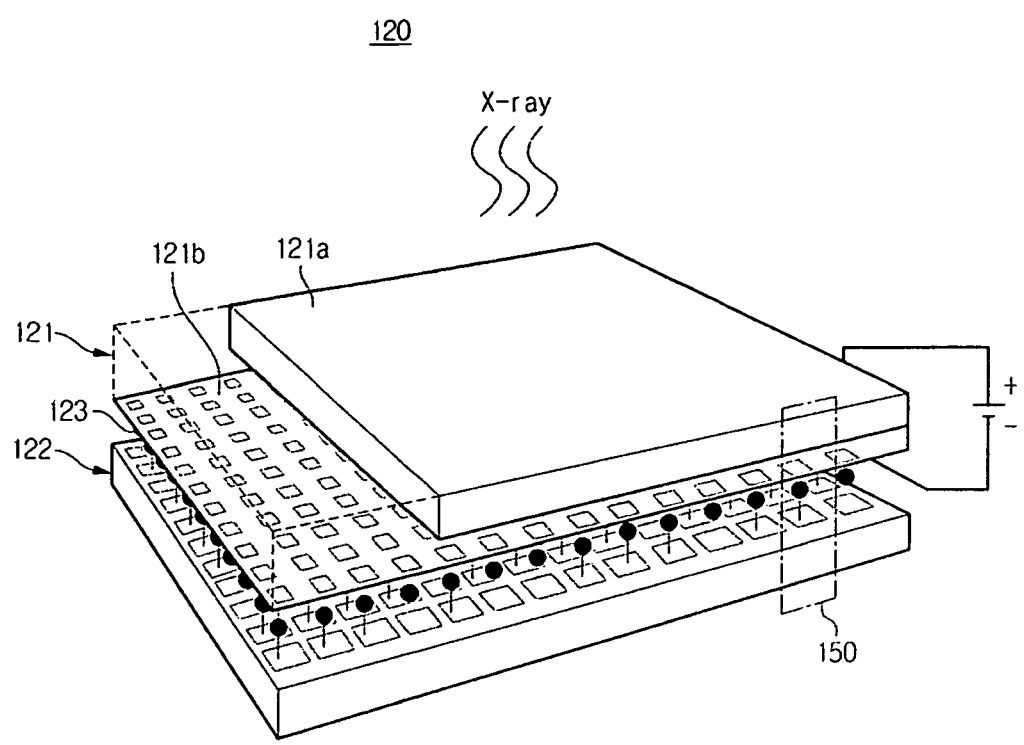
FIG. 8 is a schematic diagram illustrating a structure of an X-ray detector.

FIG. 8 is a schematic diagram illustrating a structure of an X-ray detector.

Referring to FIG. 8, the X-ray detector 120 may include a light-receiving element 121 that detects X-rays to generate electrical signals and a read-out circuit 122 that reads out the generated electrical signals.

As the light-receiving element 121, a single crystal semiconductor material may be used in order to ensure a high resolution, a fast response time, and a high dynamic range with low energy and a small dose, and in this instance, Ge, CdTe, CdZnTe, GaAs, or the like may be used as the single crystal semiconductor material.

The light-receiving element 121 may form a PIN photodiode in which a p-type semiconductor substrate 121b with a 2D array structure is joined in a lower portion of a high-resistance n-type semiconductor substrate 121a.

The read-out circuit 122 using a CMOS process may form a 2D array structure to be coupled with the p-type substrate 121b of the light-receiving element 121 for each pixel 150. In this instance, as the coupling method, a flip-chip bonding method in which a bump 123 such as solder (PbSn), indium (In), or the like is formed and then is compressed by performing reflow on the bump 123 and applying heat to the bump 123 may be used. However, the above-described structure is merely an example, and the structure of the X-ray detector 120 is not limited thereto.

The image processing unit 500 receives X-ray signals from the X-ray detector 120 or the storage unit 400, and generates at least one X-ray image using the received X-ray signals. The image processing unit 500 will be described in more detail with reference to FIGS. 9 to 14.

Figure 9:
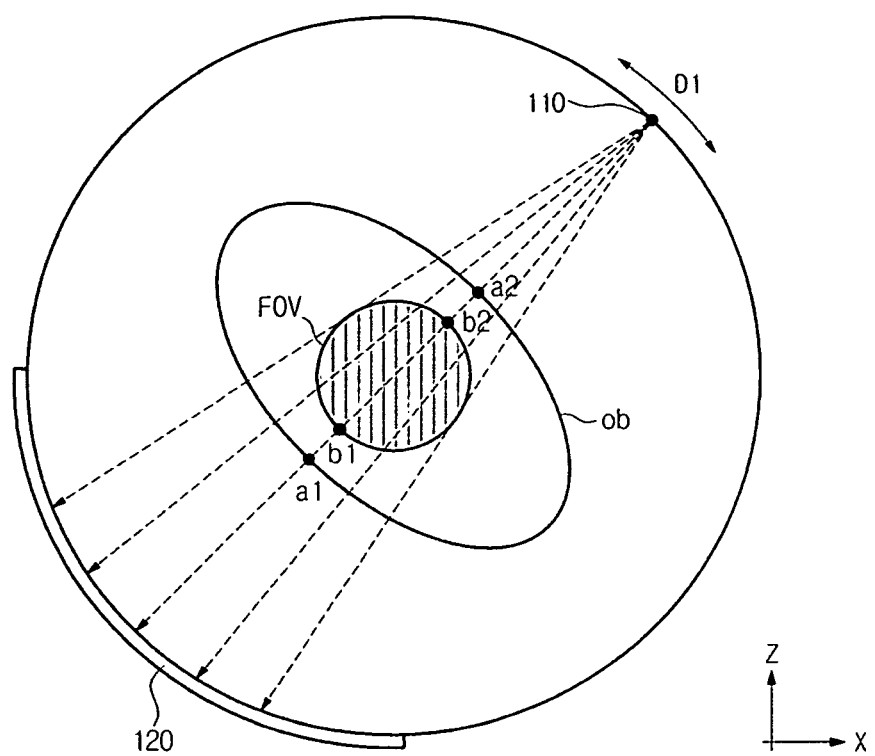
FIGS. 9 and 10 are diagrams for describing an example of X-ray radiation on a field of view (FOV)
Figure 10:
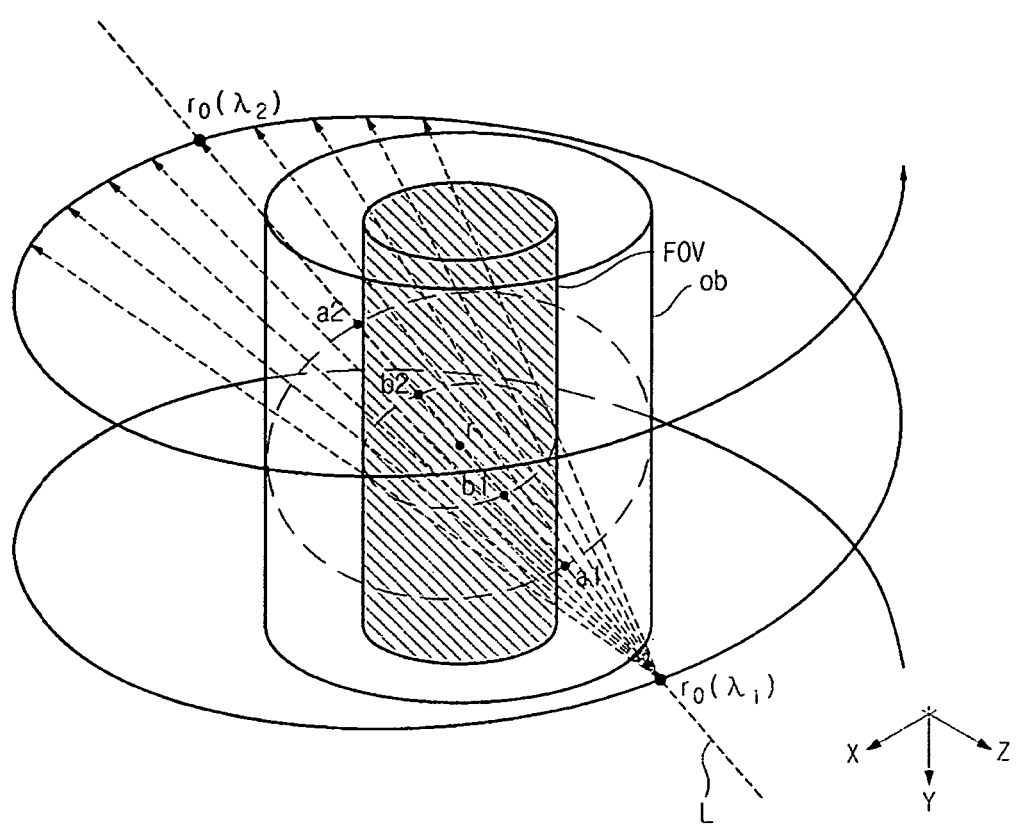

FIGS. 9 and 10 are diagrams for describing an example of X-ray radiation on an FOV.

Specifically, FIG. 9 is a diagram viewed from a plane (that is, x-z plane) formed by an X-axis and a Z-axis when X-rays are radiated by the X-ray source in FIG. 5, and FIG. 10 is a diagram obtained by extracting a part of a moving path of the X-ray source in FIG. 5.

In FIGS. 9 and 10, an example in which a partial region inside an object (ob) is set as an FOV is shown. This feature may be applied to not only a case in which the partial region of the object (ob) is set as the FOV according to a user's command, but also a case in which the partial region of the object (ob) is set as the FOV because a size of the X-ray detector 120 is relatively smaller than the object (ob).

As shown in FIG. 9, X-rays radiated from the X-ray source 110 are transmitted through the FOV inside the object (ob) to be detected by the X-ray detector 120. As described above, the X-ray source 110 may be moved in the direction D1, and thereby rotationally moved around the object (ob). In addition, the X-ray detector 120 is rotationally moved in such a manner as to be symmetrically with the X-ray source 110, and receives the X-rays radiated from the X-ray source 110.

Since the table 190 is also moved in the direction D2 while the X-ray source 110 and the X-ray detector 120 are rotating, the moving path of the X-ray source 110 and the X-ray detector 120 forms a spiral trajectory as shown in FIG. 10. A line L (hereinafter, referred to as "pi line") shown in FIG. 10 is a line that connects two arbitrary points r0($\lambda$1) and r0($\lambda$2) satisfying 0<$\lambda$2−$\lambda$1<2$\pi$ (here, $\lambda$1 and $\lambda$2 are rotation angles of the X-ray source) on the spiral trajectory, and solely exists with respect to an arbitrary point r of the FOV. The image processing unit 500 performs image restoration on the pi line to generate an X-ray image, and this feature will be described later.

In addition, as shown in FIGS. 9 and 10, points where the pi line crosses the outline of the object (ob) may be referred to as points a1 and a2, and points where the pi line crosses the outline of the FOV may be referred to as points b1 and b2.

The image processing unit 500 may first acquire a projected image with respect to the FOV using X-ray signals. The image processing unit 500 may generate a back projected image by performing back projection on the projected image, and in this instance, a derivative process may be included. That is, the image processing unit 500 may generate the back projected image using a derivative back projection (DBP) method. In addition, the image processing unit 500 may generate a restored image for the FOV using the back projected image, and further perform post-processing on the restored image. For example, the image processing unit 500 may correct brightness, luminance, contrast, or sharpness of a whole or a part of the restored image. The image post-processing may be performed in accordance with a user's instruction or command or a predetermined method.

The image processing unit 500 may transmit the X-ray image, that is, the restored image or an image obtained by performing post-processing on the restored image to the display unit 220, so that a user may confirm the X-ray image. The image processing unit 500 may transmit the acquired X-ray image to the storage unit 400 so that the storage unit 400 may temporarily or non-temporarily store the X-ray image.

Figure 11:
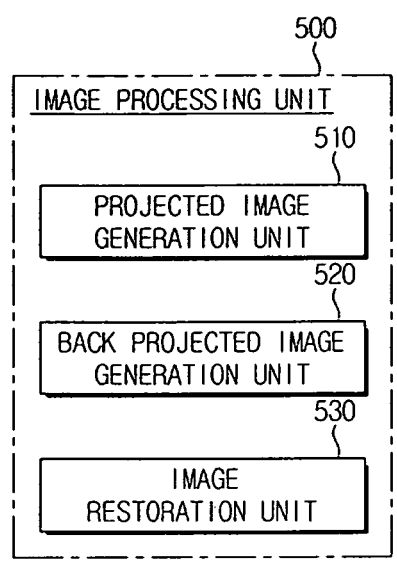
FIG. 11 is a configuration diagram illustrating an image processor in accordance with an exemplary embodiment.

FIG. 11 is a configuration diagram illustrating an image processing unit in accordance with an exemplary embodiment.

Referring to FIG. 11, the image processing unit 500 (e.g., image processor) may include a projected image generation unit 510 (e.g., projected image generator), a back projected image generation unit 520 (e.g., back projected image generator), and an image restoration unit 530 (e.g., image restorer). The projected image generation unit 510, the back projected image generation unit 520, and the image restoration unit 530 may be provided in a single processor or a single device, or separately provided in a plurality of processors or a plurality of devices.

The projected image generation unit 510 receives the X-ray signals output from the X-ray detector 120 and generates a projected image for an FOV.

The back projected image generation unit 520 calculates a DBP result value using a DBP method with respect to the projected image generated from the projected image generation unit 510, and generates a back projected image. The back projected image generation unit 520 may generate a back projected image using the following Equation 1.

$$g(r) = -\frac{1}{2\pi} \int_{\lambda_1}^{\lambda_2} \frac{d\lambda}{|r - r_0(\lambda)|} \frac{\partial}{\partial q} p(r_0(q), \beta(\lambda, r)) \Big|_{q=\lambda}$$ [Equation 1]

where $0 < \lambda_2 - \lambda_1 < 2\pi, \beta(\lambda, r) \in$

Here, r denotes an arbitrary point on an FOV, q denotes a rotation angle of the X-ray source 110, r0(q) denotes a trajectory vector, r0(λ1) and r0(λ2) denote points that cross a pi line of r, that is, a trajectory of the X-ray source 110, p(r0(q), (β(λ,r)) denotes a projected image, g(r) denotes a back projected image, and $S^2$ denotes a unit sphere.

In this instance, the back projected image g(r) may be represented in a one-dimensional manner based on the following Equation 2, with respect to t∈[0,1] that represents a position on the pi line of r in proportion.

$$x = \left(t - \frac{1}{2}\right)|r_0(\lambda_2) - r_0(\lambda_1)|$$ [Equation 2]

That is, the back projected image generation unit 520 may acquire a back projected image g(x) represented in a one-dimensional manner using Equations 1 and 2.

The image restoration unit 530 generates a restored image for each frequency component with respect to the back projected image. As an example, the image restoration unit 530 may divide the back projected image into a low frequency component and a high frequency component, and generate a restored image (hereinafter, also referred to as "low frequency image") for the low frequency component and a restored image (hereinafter, also referred to as "high frequency image") for the high frequency component. The image restoration unit 530 may acquire a final restored image for the FOV by synthesizing the restored image for each frequency component. As described above, the image restoration unit 530 may acquire the final restored image by synthesizing the low frequency image and the high frequency image. The image restoration unit 530 may further perform post-processing on the restored image of the FOV.

Figure 12:
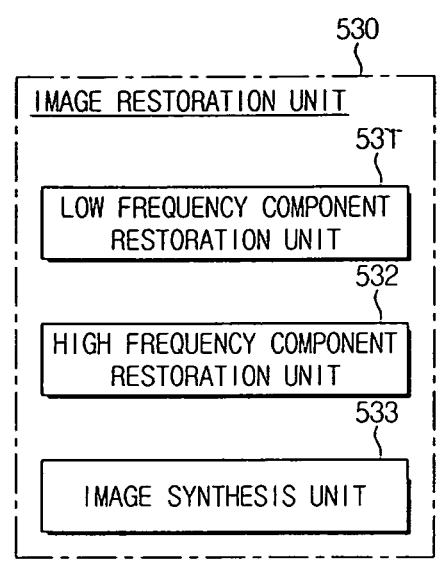
FIG. 12 is a configuration diagram illustrating an image restorer in accordance with an exemplary embodiment.

FIG. 12 is a configuration diagram illustrating an image restoration unit in accordance with an exemplary embodiment.

Referring to FIG. 12, the image restoration unit 530 may include a low frequency component restoration unit 531 (e.g., low frequency component restorer), a high frequency component restoration unit 532 (e.g., high frequency component restorer), and an image synthesis unit 533 (e.g., image synthesizer). In the image restoration unit 530, the low frequency component restoration unit 531, the high frequency component restoration unit 532, and the image synthesis unit 533 may be provided in a single processor or a single device, or separately provided in a plurality of processors or a plurality of devices.

The low frequency component restoration unit 531 extracts a low frequency component from the back projected image generated from the back projected image generation unit 520, and generates a restored image for the extracted low frequency component. A process of generating the restored image for the low frequency component will be described in more detail with reference to FIGS. 13 to 15.

Figure 13:
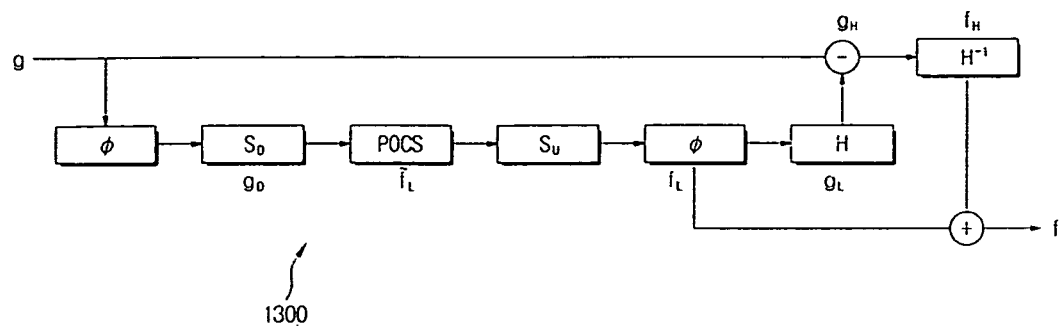
FIG. 13 is a diagram illustrating a process in which a restored image is generated by an image restorer in accordance with an exemplary embodiment.
Figure 14:
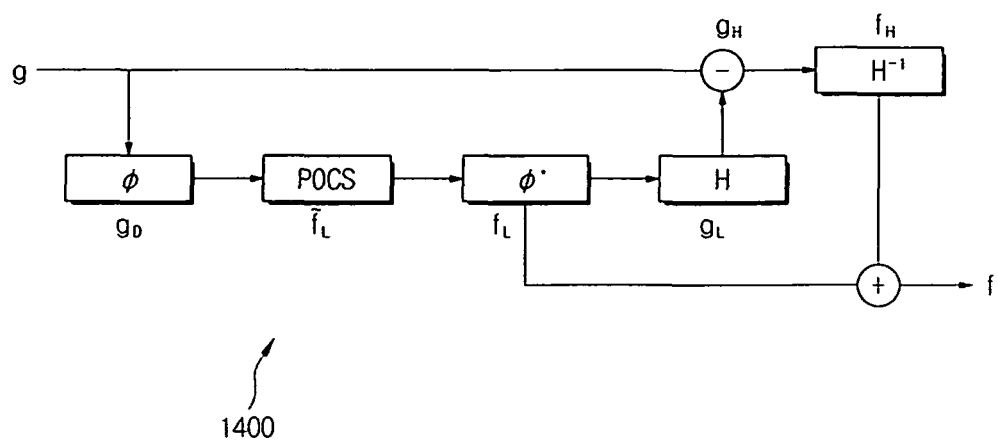
FIG. 14 is a diagram illustrating a process in which a restored image is generated by an image restorer in accordance with another exemplary embodiment.
Figure 15:
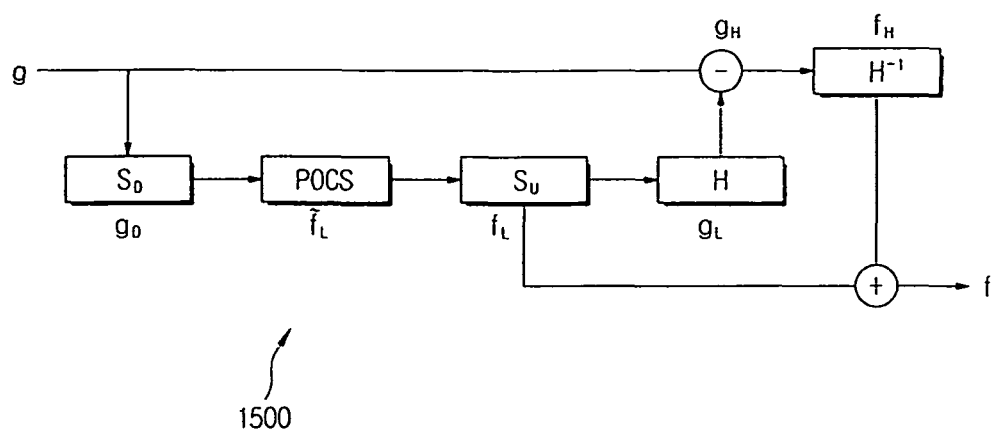
FIG. 15 is a diagram illustrating a process in which a restored image is generated by an image restorer in accordance with still another exemplary embodiment.

FIG. 13 is a diagram illustrating a process 1300 in which a restored image is generated by an image restoration unit in accordance with an exemplary embodiment, FIG. 14 is a diagram illustrating a process 1400 in which a restored image is generated by an image restoration unit in accordance with another exemplary embodiment, and FIG. 15 is a diagram illustrating a process 1500 in which a restored image is generated by an image restoration unit in accordance with still another exemplary embodiment.

Referring to FIGS. 13 to 15, the low frequency component restoration unit 531 first extracts a low frequency component by performing filtering using a low pass filter (LPF) or down sampling on the back projected image g(x). In this instance, the LPF may be defined as φ, down sampling may be defined as $S_D$, and the low frequency component may be defined as $g_D(x)$.

As an example, the low frequency component restoration unit 531 may perform filtering on the back projected image g(x) using the LPF φ as shown in FIG. 13 and perform down sampling on the filtered image, thereby acquiring the low frequency component $g_D(x)$ of g(x). In this instance, a wavelet transform method may be used. In a case of general wavelet transform, an LPF and a high pass filter (HPF) are applied to a given image, and wavelet decomposition that performs down sampling on each filtered image is performed. On the other hand, in a case in which the low frequency component restoration unit 531 uses the wavelet transform method, only the LPF φ may be applied to the back projected image g(x) when wavelet decomposition is performed, and down sampling ($S_D$) may be performed on only the filtered image.

As another example, the low frequency component restoration unit 531 may acquire the low frequency component $g_D(x)$ by performing filtering on the back projected image g(x) using the LPF φ, as shown in FIG. 14. As still another example, the low frequency component restoration unit 531 may acquire the low frequency component $g_D(x)$ by performing down sampling $S_D$ on g(x) as shown in FIG. 15.

The low frequency component restoration unit 531 may generate a low frequency image by performing image restoration on the low frequency component $g_D(x)$, and the generated low frequency image may be defined as $f_L(x)$. The low frequency component restoration unit 531 may generate the low frequency image $f_L(x)$ for $g_D(x)$ using a regulation function. Here, as the regulation function, total variation (TV) may be applied. In addition, the low frequency component restoration unit 531 may generate the low frequency image $f_L(x)$ using a repetitive restoration method.

The low frequency component restoration unit 531 may perform image restoration on $g_D(x)$ using the regulation function and the repetitive restoration method or the repetitive restoration method to which the regulation function is applied. For example, the low frequency component restoration unit 531 may use the repetitive restoration method to which TV is applied, and the repetitive restoration method to which TV is applied may be implemented through a projection onto convex set (POCS).

Hereinafter, in descriptions of FIGS. 13 to 15, a case of using POCS when performing image restoration will be described. In addition, an image in which POCS is applied to the low frequency component $g_D(x)$ may be defined as $\tilde{f}_L(x)$ separately from the low frequency image $f_L(x)$. The POCS method for generating $\tilde{f}_L(x)$ may be represented as the following Equation 3.

$$\tilde{f_{L_k}}(x) = P_{c5} \cdot P_{c4} \cdot P_{c3} \cdot P_{c2} \cdot P_{c1} \cdot \tilde{f_{L_{k-1}}}(x), \quad \text{[Equation 3]}$$

where $k$, $$C1 = \{\tilde{f_L}(x) \in L^2(R) : \tilde{f_L}(x) = 0, x \notin \{a_1, a_2\}\},$$

$$C2 = \{\tilde{f_L}(x) \in L^2(R) : H\tilde{f_L}(x) = g_D(x), x \in \{b_1, b_2\}\},$$

$$C3 = \{\tilde{f_L}(x) \in L^2(R) : TV(\tilde{f_L}(x)) \le c,$$

$$C4 = \{\tilde{f_L}(x) \in L^2(R) : \frac{1}{\pi}\int_{a1}^{a2} dx\, \tilde{f_L}(x) =$$

$$C_f = \frac{1}{\pi} p(r_0(\lambda), \beta(\lambda, r))\},$$

$$C5 = \{\tilde{f_L}(x) \in L^2(R) : \tilde{f_L}(x) \ge 0, x \in \{a_1, a_2\}\}$$

Here, N denotes a positive integer, and an initial value $f_{L\_0}(x)$ is an arbitrary value that is defined in advance by a user or defined according to a setting of a system. $P_{c1}$, $P_{c2}$, $P_{c3}$, $P_{c4}$, and $P_{c5}$ respectively denote projections according to C1, C2, C3, C4, and C5, $L^2(R)$ denotes an L2-norm, H denotes a Hilbert transform, and TV denotes total variation. In addition, c is a value close to "0" so that $TV(f_L(x))$ can be minimized, and may be defined in advance by the user or determined according to a setting of the system.

In FIG. 13, LPF φ and down sampling $S_D$ have been performed, and therefore the low frequency image $f_L(x)$ for $g_D(x)$ may be generated by performing up sampling (hereinafter, referred to as "$S_U$") and conjugate of the LPF φ, that is, φ* with respect to $\tilde{f}_L(x)$. When the low frequency component restoration unit 531 performs wavelet decomposition using the wavelet transform method, up sampling Su is performed on $\tilde{f}_L(x)$, and wavelet decomposition that applies only conjugate φ* of the LPF to this.

In FIG. 14, the LPF φ has been performed, and therefore the low frequency image $f_L(x)$ may be generated by performing conjugate φ* of the LPF on $\tilde{f}_L(x)$. In addition, in FIG. 15, down sampling has been performed, and therefore the low frequency image $f_L(x)$ may be generated by performing up sampling $S_U$ on $\tilde{f}_L(x)$.

As described above, the low frequency component restoration unit 531 acquires the low frequency component $g_D(x)$ through LPF φ or down sampling $S_D$, and generates a restored image for the low frequency component $g_D(x)$, that is, the low frequency image $f_L(x)$ using the regulation function or the repetitive restoration method.

The high frequency component restoration unit 532 extracts a high frequency component of the back projected image g(x) using the low frequency image $f_L(x)$ generated from the low frequency component restoration unit 531, and generates a restored image for the extracted high frequency component. In this instance, the high frequency component of the back projected image g(x) is defined as $g_H(x)$, and the restored image for the high frequency component $g_H(x)$ is defined as $f_H(x)$.

First, the high frequency component restoration unit 532 may acquire the high frequency component $g_H(x)$ using the following Equation 4.

$$g(x) = \frac{1}{\pi} P.V. \cdot \int_{-\infty}^{\infty} \frac{dx'}{x-x'} f(x') = Hf(x) \quad \text{[Equation 4]}$$

Here, f(x) denotes a restored image, g(x) denotes a back projected image, P.V. denotes a Cauchy principal value, and H denotes Hilbert transform.

The high frequency component restoration unit 532 may calculate $Hf_L(x)$ for the low frequency image $f_L(x)$, and acquire $g_L(x)$ corresponding to $f_L(x)$ using Equation 4. That is, the high frequency component restoration unit 532 may acquire $g_L(x)$ in which $g_L(x)=Hf_L(x)$ is achieved. In this manner, $g_L(x)$ acquired from the low frequency image $f_L(x)$ may be also a low frequency component of the back projected image g(x), and $g_L(x)$ may be the same as or different from $g_D(x)$ described above.

As shown in FIGS. 13 to 15, the high frequency component restoration unit 532 may acquire the high frequency component $g_H(x)$ of g(x) using a difference between the back projected image g(x) and the low frequency component $g_L(x)$. That is, $g_H(x)=g(x)-g_L(x)$ is achieved.

According to an exemplary embodiment, by using Equation 4 and a Bedrosian equation relationship of Hilbert transform, the following Equation 5 may be obtained.

$$w(x) \cdot g_H(x) = w(x) \cdot Hf_H(x) = H\{w(x) \cdot f_H(x)\} \quad \text{[Equation 5]}$$

Here, w(x) denotes a window function corresponding to the low frequency component $g_L(x)$. Specifically, when the low frequency component $g_L(x)$ and the high frequency component $g_H(x)$ are obtained on the basis of a frequency $\omega_0$ for the projected image g(x), that is, when $g_L(x)$ disappears for the frequency $\omega_0$ or higher and $g_H(x)$ disappears for a frequency lower than the frequency $\omega_0$, w(x) is a window function in which disappearance is performed for the frequency $\omega_0$ or higher. The window function w(x) may be defined in advance by the user or determined according to a setting of the system. In addition, the window function w(x) may have various shapes such as a rectangle, a triangle, and the like.

In Equation 5, a relationship of $w(x) \cdot g_H(x)$ and $w(x) \cdot Hf_H(x)$ may be achieved by Equation 4, and a relationship of $w(x) \cdot Hf_H(x)$ and $H\{w(x) \cdot f_H(x)\}$ may be achieved by a Bedrosian equation relation of a Hilbert transform. In addition, in Equation 5, from a relationship of $w(x) \cdot g_H(x)$ and $H\{w(x) \cdot f_H(x)\}$ and a relationship between a Hilbert transform and an inverse Hilbert transform, that is, $H^{-1}=-H$, the following Equation 6 may be obtained.

$$f_H(x) = \frac{H^{-1}\{w(x) \cdot g_H(x)\}}{w(x)} = \frac{-H\{w(x) \cdot g_H(x)\}}{w(x)} \quad \text{[Equation 6]}$$

The high frequency component restoration unit 532 generates a high frequency image $f_H(x)$ that is a restored image for the high frequency component $g_H(x)$ using Equation 6.

The image synthesis unit 533 generates a final restored image f(x) by synthesizing the low frequency image $f_L(x)$ generated from the low frequency component restoration unit 531 and the high frequency image $f_H(x)$ generated from the high frequency component restoration unit 532, as shown in FIGS. 13 to 15. That is, $f(x)=f_L(x)+f_H(x)$ is achieved.

The image restoration unit 530 may generate the restored image f(x) for the FOV through the low frequency component restoration unit 531, the high frequency component restoration unit 532, and the image synthesis unit 533 as described above, and the image processing unit 500 may transmit the restored image f(x) as is to the display unit 220, or perform post-processing on the restored image f(x) and then transmit the image subjected to post-processing to the display unit 220. The X-ray image, that is, the restored image f(x) or the image obtained by performing post-processing on the restored image f(x), may be stored in the storage unit 400.

The storage unit 400 stores data and a program for operations of the X-ray imaging apparatus 1.

As an example of data storage, the storage unit 400 may store a rotation rate or rotation speed of the gantry 102, radiation frequency or radiation of the X-ray source 110, a moving speed of the table 190, and the like, when X-ray radiography is performed. The storage unit 400 may store the X-ray signals acquired from the X-ray detector 120, the restored image f(x) acquired from the image restoration unit 530, the X-ray image acquired from the image processing unit 500, and the like.

As an example of program storage, the storage unit 400 may store a program for generating a projected image p(r0(q), δ(Δ,r)), a program for generating the back projected image g(x), a program for generating the low frequency image $f_L(x)$ and the high frequency image $f_H(x)$, a program for generating the restored image f(x), a program for image post-processing, and the like.

Such a storage unit 400 may include a storage medium of at least one type among a flash memory, a hard disk, a multimedia card micro type storage medium, a card memory (for example, an SD or XD memory, etc.), a random access memory (RAM), a static RAM (SRAM), a read-only memory (ROM), an electrically erasable programmable ROM (EEPROM), a programmable ROM (PROM), a magnetic memory, a magnetic disk, and an optical disc. However, the storage unit 400 is not limited thereto, and may be implemented in other arbitrary forms which are well known in the art. In addition, a consumer electronic apparatus 100 may operate a web storage that performs a storage function on the Internet.

The control unit 300 may generate a predetermined control command and transmit the generated control command to the X-ray source 110, the X-ray detector 120, the storage unit 400, the image processing unit 500, or the like, thereby controlling overall operations of the X-ray imaging apparatus 1.

The control unit 300 may control the operations of the X-ray imaging apparatus 1 in accordance with a user's instruction or command input from the input unit 210, or in accordance with a predetermined setting.

For example, the control unit 300 may control rotation of the gantry 102, rotation of the X-ray source 110 and the X-ray detector 120, or movement of the table 190. The control unit 300 may generate control signals and transmit the generated control signals to the X-ray source 110 so that the X-ray source 110 applies power of a predetermined voltage to the X-ray tube 111 to generate X-rays with predetermined energy. In addition, the control unit 300 may control various operations of the X-ray detector 120 such as a read-out operation of the X-rays.

The control unit 300 may control the X-ray signals of the X-ray detector 120 to be transmitted to the storage unit 400, or control the storage unit 400 to temporarily or non-temporarily store the X-ray signals.

The control unit 300 may transmit various control signals for generating the restored image f(x) to the image processing unit 500. For example, the control unit 300 may control the image processing unit 500 so that the low frequency image $f_L(x)$ is generated according to a POCS algorithm as shown in Equation 3, the high frequency image $f_H(x)$ is generated using Equation 7, or the restored image is generated through image synthesis.

The control unit 300 may generate control signals so that the restored image f(x) or the X-ray image is displayed through the display unit 220.

The control unit 300 may be implemented as a variety of processors including at least one chip in which an integrated circuit is formed. Such a central processing unit (CPU) may be provided in a single processor or a single device, or may be separately provided in a plurality of processors or a plurality of devices.

Figure 16:
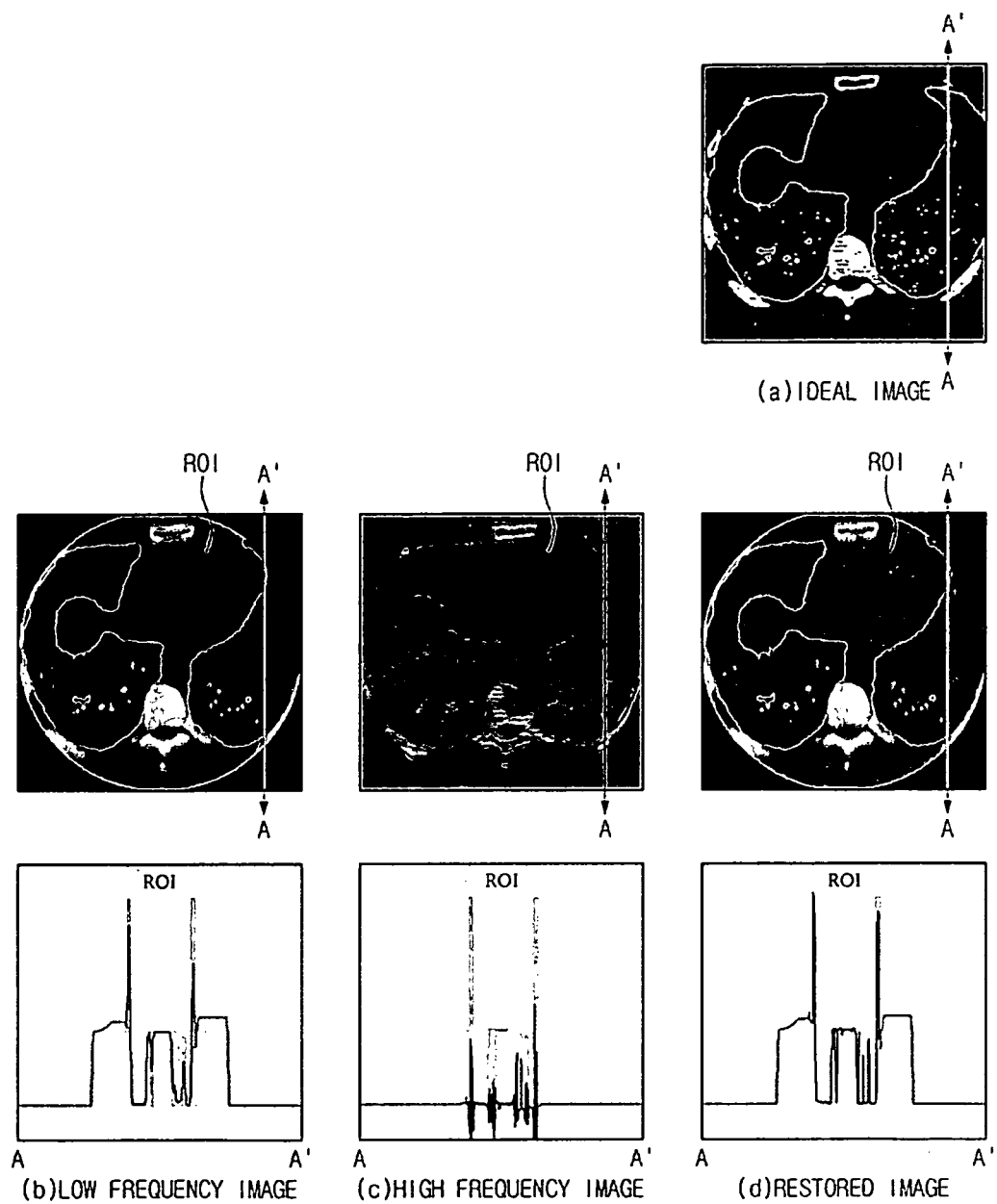
FIG. 16 is a diagram illustrating a restored image generated by an X-ray imaging apparatus.

FIG. 16 is a diagram illustrating a restored image generated by an X-ray imaging apparatus.

FIG. 16, an image (a) indicates an ideal image desired to be acquired. In addition, an upper image of (b) indicates a low frequency image $f_L(x)$, and a lower image of (b) (graph) indicates signal intensity of the low frequency image taken along the A-A' line. Similarly, an upper image of (c) indicates a high frequency image $f_H(x)$ and a lower image of (c) (graph) indicates a signal intensity of the high frequency image taken along the A-A' line. An upper image of (d) indicates a restored image f(x) obtained by synthesizing the low frequency image $f_L(x)$ and the high frequency image $f_H(x)$, and a lower image of (d) (graph) indicates a signal intensity of the restored image taken along the A-A' line.

In addition, dotted lines in the lower images (graphs) of (b), (c), and (d) indicate an intensity of signals of the ideal image taken along the A-A' line, a solid line of (b) indicates a signal intensity of the low frequency image taken along the A-A' line, a solid line of (c) indicates a signal intensity of the high frequency image taken along the A-A' line, and a solid line of (d) indicates a signal intensity of the restored image taken along the A-A' line, and therefore the ideal image and each image generated from the image processing unit 500 may be compared.

As shown in (b), (c), and (d), an FOV may be set as a region of interest (ROI) inside an object (ob). When comparing the ideal image and the restored image f(x), it can be seen that mutually similar shapes and boundaries are shown in the FOV or the ROI. As shown in the graph of (d), the signal intensity of the restored image may have almost the same shape as the signal intensity of the ideal image in the FOV or the ROI.

The X-ray imaging apparatus that generates the restored image f(x) or the X-ray image for the FOV has been described above based on the exemplified control block diagram, and a control method for the X-ray imaging apparatus will be described with reference to FIG. 17.

Figure 17:
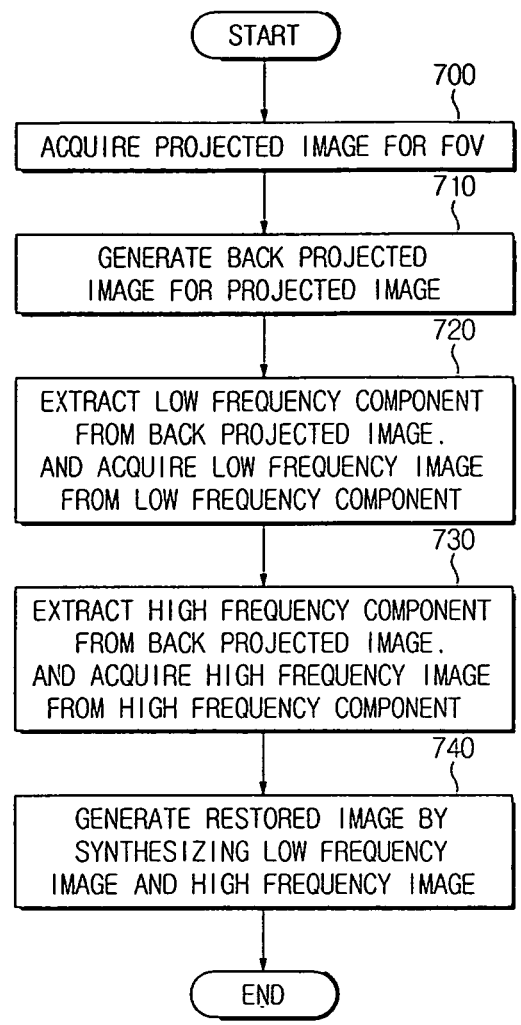
FIG. 17 is a flowchart illustrating a control method for an X-ray imaging apparatus in accordance with an exemplary embodiment.

FIG. 17 is a flowchart illustrating a control method for an X-ray imaging apparatus in accordance with an exemplary embodiment.

Referring to FIG. 17, in operation 700, the X-ray imaging apparatus 1 generates a projected image for an FOV.

Specifically, the X-ray imaging apparatus 1 rotates the gantry 102 in a direction D1 and moves the table 190 in a direction D2, and therefore a moving path of the X-ray source 110 and the X-ray detector 120 forms a spiral trajectory based on the FOV. The X-ray source 110 radiates X-rays while moving along the spiral trajectory, and the X-ray detector 120 detects X-rays transmitted through the FOV. The image processing unit 500 may generate the projected image for the FOV based on X-ray signals output from the X-ray detector 120.

Next, in operation 710, a back projected image for the projected image is generated.

The image processing unit 500 may generate the back projected image for the projected image using a DBP method. The image processing unit 500 may acquire the back projected image g(x) that is represented in a one-dimensional manner using the above-described Equations 1 and 2.

In operation 720, the image processing unit 500 extracts a low frequency component from the back projected image, and generates a low frequency image from the extracted low frequency component.

Specifically, the image processing unit 500 may extract the low frequency component $g_D(x)$ by performing filtering using the LPF $\varphi$ or down sampling $S_D$ on the back projected image g(x). In addition, the image processing unit 500 may perform image restoration on $g_D(x)$ using a regulation function and a repetitive restoration method or a repetitive restoration method to which the regulation function is applied. For example, the image processing unit 500 applies a POCS shown in Equation 3 to $g_D(x)$, and generates $\tilde{f}_L(x)$. The image processing unit 500 may perform up sampling or conjugate $\varphi^*$ of the LPF with respect to $\tilde{f}_L(x)$ in response to the LPF $\varphi$ or down sampling $S_D$, and thereby generate the low frequency image $f_L(x)$ for $g_D(x)$.

In operation 730, when the low frequency image $f_L(x)$ is generated, the image processing unit 500 extracts a high frequency component from the back projected image using the generated low frequency image $f_L(x)$, and generates a high frequency image from the extracted high frequency component.

Specifically, the image processing unit 500 may repeatedly acquire the low frequency component $g_L(x)$ of the back projected image g(x) through Equation 4, that is, a Hilbert transform relationship. That is, $g_L(x)$ in which $g_L(x)=Hf_L(x)$ is achieved may be acquired. As described above, $g_L(x)$ may be the same as or different from the initially generated low frequency component $g_D(x)$.

The image processing unit 500 may acquire the high frequency component $g_H(x)$ of g(x) using a difference between the back projected image g(x) and the low frequency component $g_L(x)$. In addition, a high frequency image $f_H(x)$ may be generated using the high frequency component $g_H(x)$, a window function w(x) corresponding to the low frequency component $g_L(x)$, and Equation 6.

In operation 740, when the high frequency image $f_H(x)$ is generated, the image processing unit 500 generates a restored image f(x) for the FOV by synthesizing the low frequency image and the high frequency image.

The image processing unit 500 may further perform post-processing on the restored image f(x). The restored image generated from the image processing unit 500 or the image obtained by performing post-processing on the restored image, that is, an X-ray image, may be displayed by the display unit 220.

Figure 18:
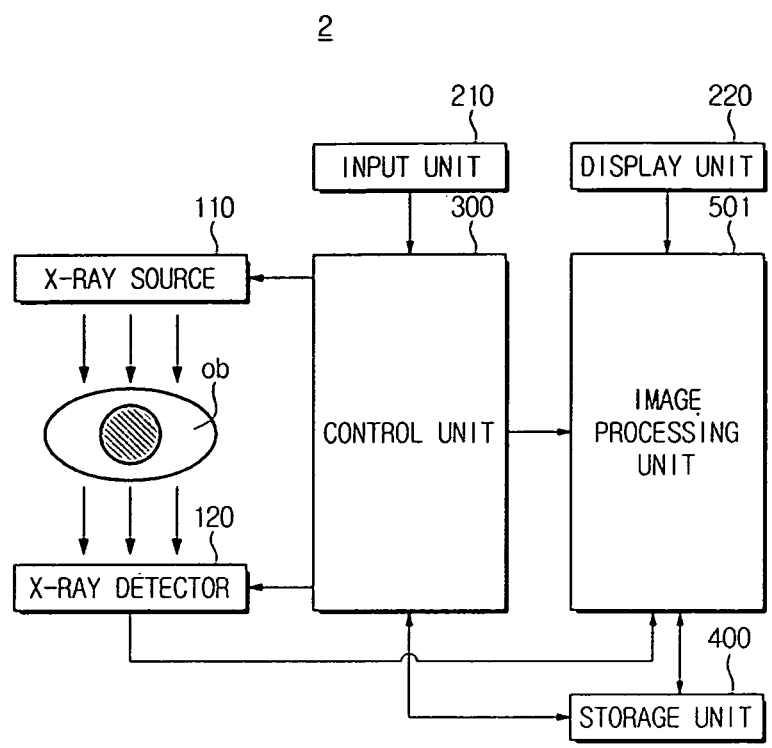
FIG. 18 is a control block diagram illustrating an X-ray imaging apparatus in accordance with another exemplary embodiment.
Figure 19:
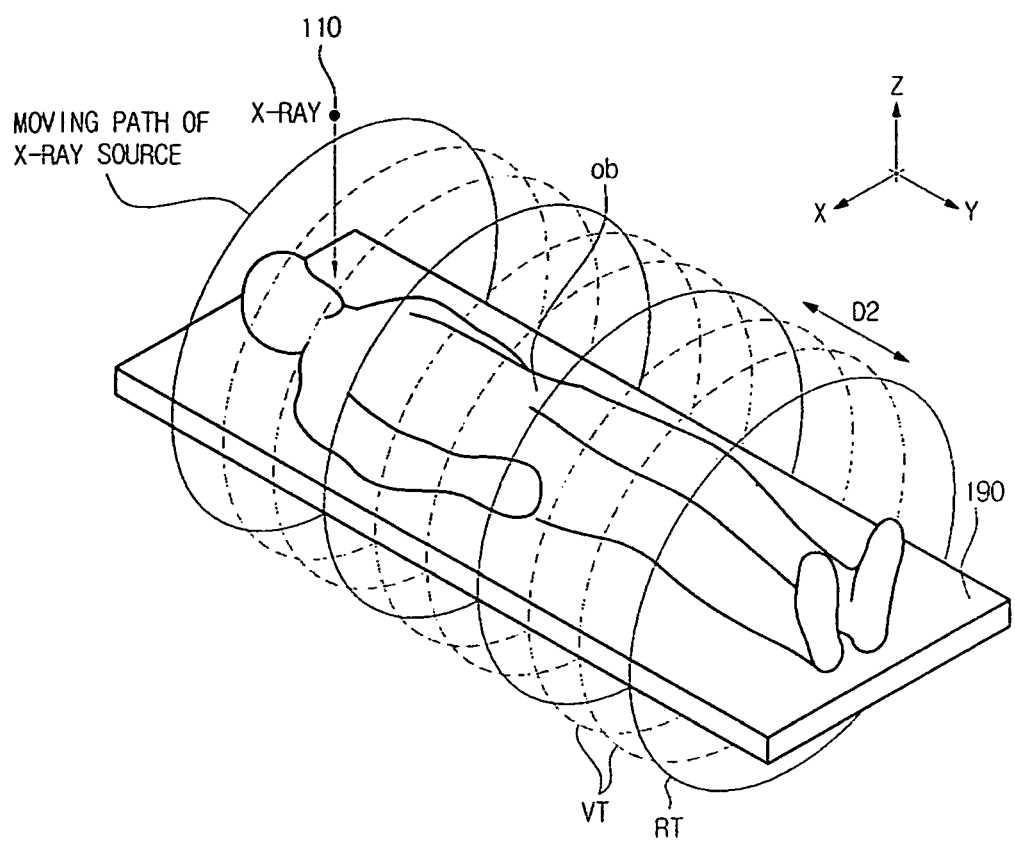
FIG. 19 is a diagram illustrating a movement trajectory of an X-ray source of an X-ray imaging apparatus in accordance with another exemplary embodiment.

FIG. 18 is a control block diagram illustrating an X-ray imaging apparatus in accordance with another exemplary embodiment, and FIG. 19 is a diagram illustrating a movement trajectory of an X-ray source of an X-ray imaging apparatus in accordance with another exemplary embodiment.

Hereinafter, the same configurations as those of the X-ray imaging apparatus 1 in accordance with an exemplary embodiment will be denoted by the same reference numerals, and thus detailed description thereof will be omitted. In addition, an X-ray imaging apparatus 2 in accordance with another exemplary embodiment may be configured in the same manner as that of the X-ray imaging apparatus 1 in accordance with an exemplary embodiment unless otherwise mentioned, and perform the same operations.

Referring to FIG. 18, the X-ray imaging apparatus 2 in accordance with the other exemplary embodiment may include an X-ray source 110, an X-ray detector 120, an input unit 210, a control unit 300, a storage unit 400, and an image processing unit 501.

The X-ray source 110 of the X-ray imaging apparatus 2 in accordance with the other exemplary embodiment may radiate X-rays to an object while moving along a circular trajectory as shown in FIG. 19.

That is, the movement of the table 190 and the movement of the gantry 102 may be separately performed. In this manner, when the movement of the table 190 and the movement of the gantry 102 are separately performed, the movement trajectory of the X-ray source 110 may form the circular trajectory as shown in FIG. 19.

When the X-ray source 110 moves along the circular trajectory in this manner, a surface on which the X-ray source 110 is actually rotated is referred to as a real orbital surface RT, and a surface other than the real orbital surface RT, i.e., a surface on which the X-ray source 110 is not actually rotated is referred to as a virtual orbital surface VT.

The X-ray detector 120 moves along the circular trajectory together with the X-ray source 110, and thereby is positioned in a direction facing the X-ray source 110. X-ray signals obtained while the X-ray detector 120 moves along the circular trajectory in this manner are transmitted to the storage unit 400 or the image processing unit 501.

The image processing unit 501 may generate a restored image using the X-ray signals output from the X-ray detector 120. As described above, a projected image may be generated from the X-ray signals, and a restored image may be generated using a back projected image generated using the projected image. A generation method of the restored image is the same as that of the image processing method of the above-described image processing unit 500, and thus detailed description thereof will be omitted.

In addition, the image processing unit 501 may generate a corrected image whose noise is corrected by correcting noise of the restored image. The noise of the restored image occurs in the virtual orbital surface VT different from the real orbital surface RT on which the X-ray source 110 is actually rotated, and occurs due to a phase difference between the X-ray source 110 and the virtual orbital surface VT.

Specifically, due to the phase difference between the X-ray source 110 and the virtual orbital surface VT, a loss frequency region LS in which a loss of frequencies occurs is present on the virtual orbital surface VT, and therefore the image processing unit 501 may correct the noise of the restored image by minimizing the loss frequency region LS. Hereinafter, the loss frequency region LS will be described in more detail.

Figure 20:
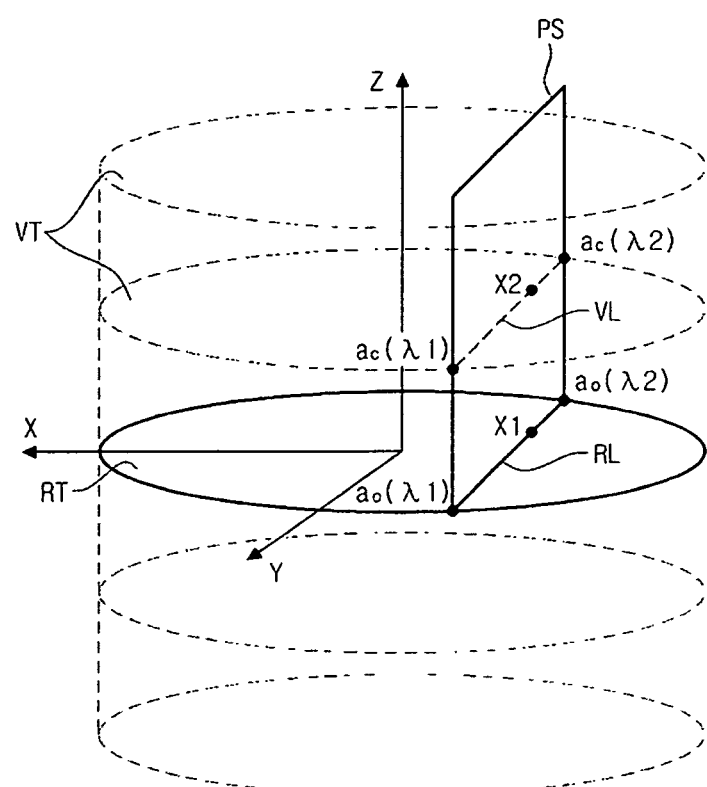
FIG. 20 is a diagram illustrating a real orbital surface and a virtual orbital surface.
Figure 21:
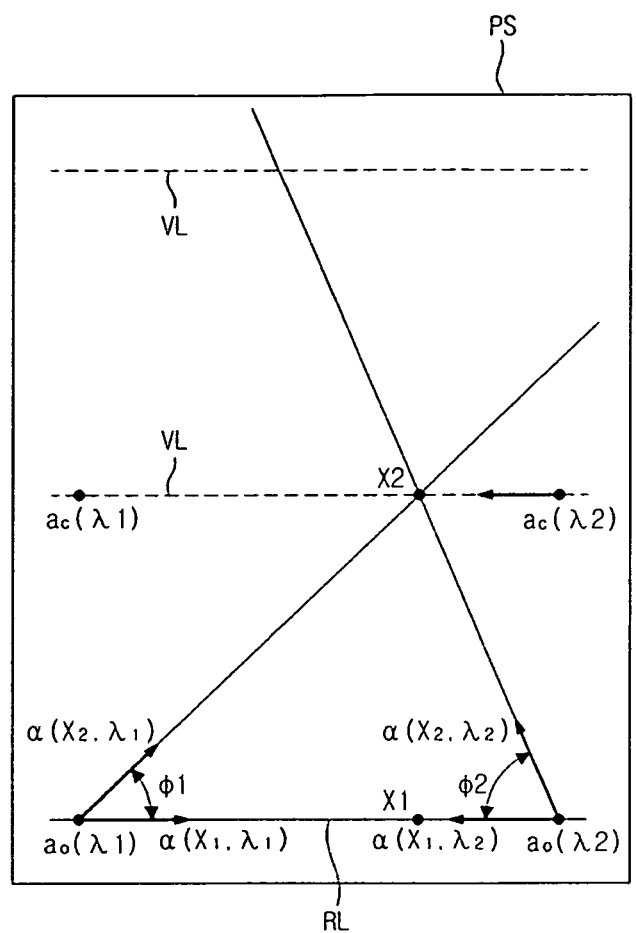
FIG. 21 is a diagram illustrating a cross section PS of an object of FIG. 20.
Figure 22:
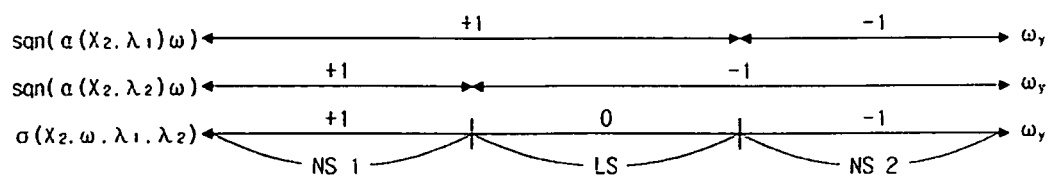
FIG. 22 is a diagram illustrating a loss frequency region.
Figure 23:
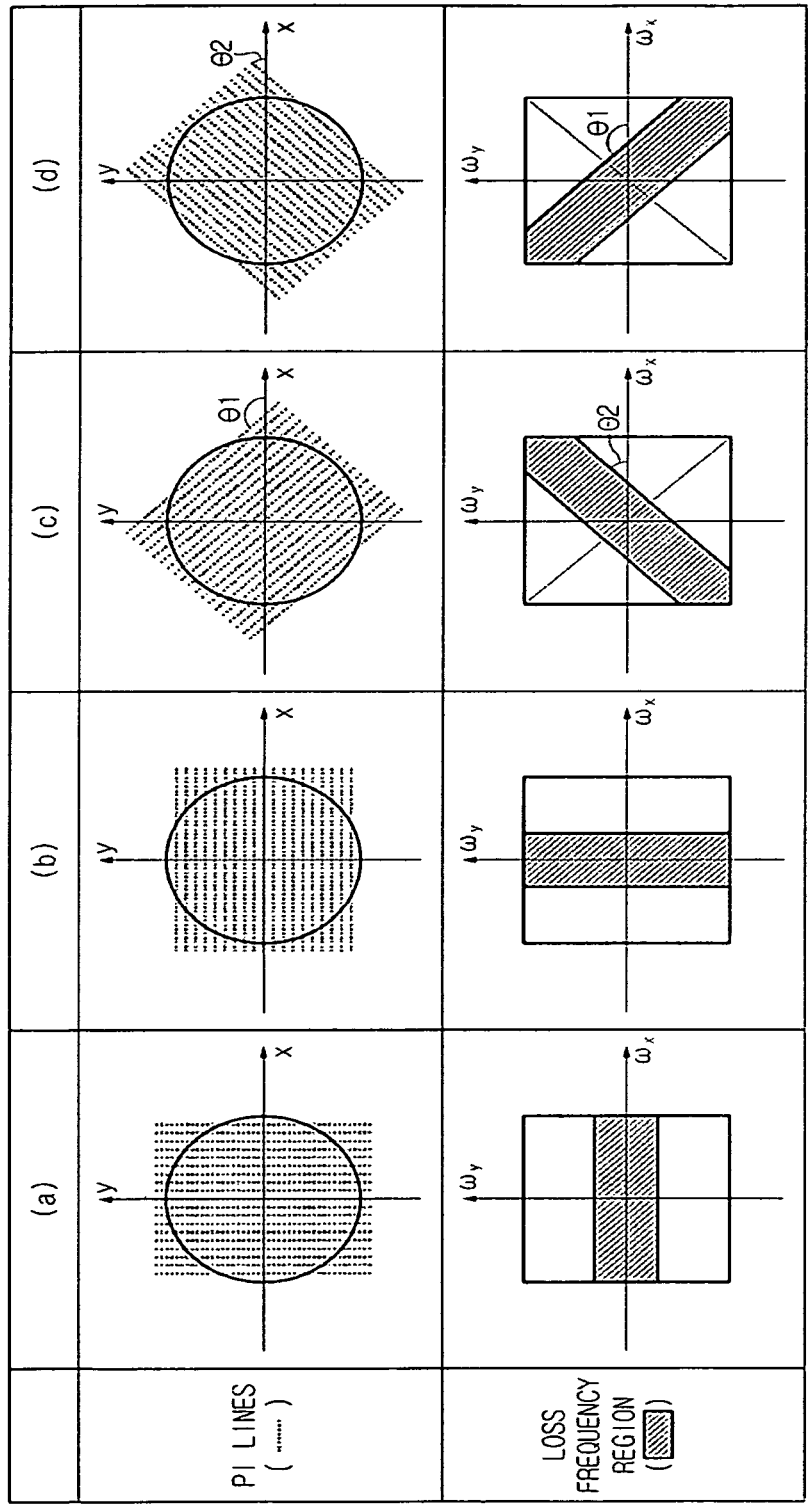
FIG. 23 is a diagram illustrating a correlation between pi lines and the loss frequency region.
Figure 24:
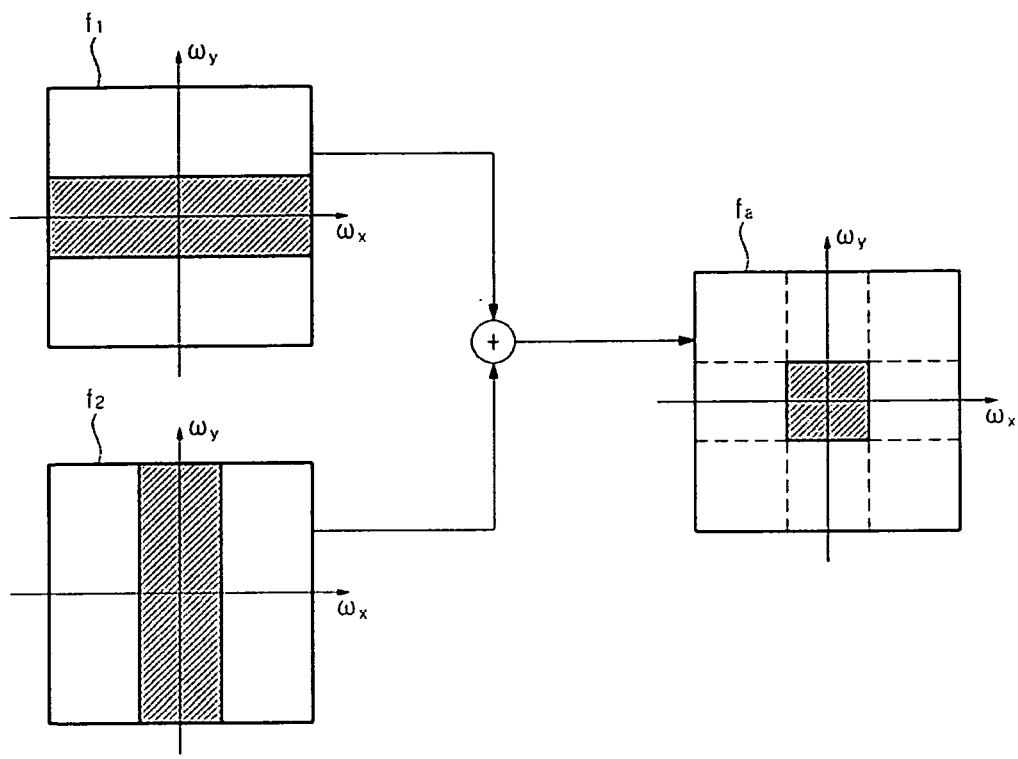
FIG. 24 is a diagram for describing a concept of generation of a corrected image.

FIG. 20 is a diagram illustrating a real orbital surface and a virtual orbital surface, FIG. 21 is a diagram illustrating a cross section PS of an object of FIG. 20, FIG. 22 is a diagram illustrating a loss frequency region LS, FIG. 23 is a diagram for describing a correlation between pi lines and a loss frequency region, and FIG. 24 is a diagram for describing a concept of generation of a corrected image.

Referring to FIGS. 20 and 21, pi lines L used for image generation may be classified into real pi lines RL which connect two arbitrary points $a_0(\lambda 1)$ and $a_0(\lambda 2)$ on the rear orbital surface RT, and virtual pi lines VL which connect two arbitrary points $a_c(\lambda 1)$ and $a_c(\lambda 2)$ on the virtual orbital surface VT.

The arbitrary point x1 of the real pi lines RL has the same phase as that of the X-ray source 110, and therefore a region in which a loss of frequencies occurs is not present in the real pi lines RL. However, the arbitrary point x2 of the virtual pi lines VL has phase differences φ1 and φ2 with respect to the X-ray source 110. Due to the phase differences φ1 and φ2, the loss frequency region LS in which frequencies are lost is present in the virtual pi lines VL.

The presence of the loss frequency region LS may be defined by the following Equation 7.

$$g(x) = \frac{1}{(2\pi)^d} \int f(x) e^{jx \cdot \omega} j\sigma(x, \omega, \lambda_1, \lambda_2) d\omega \quad \text{[Equation 7]}$$

Equation 7 represents, in the frequency domain, a back projected image g(x) represented in a one-dimensional manner. Here, x denotes an arbitrary point inside the object, f(x) denotes a projected image inside the object, w denotes a frequency component, λ1 and λ2 denote rotation angles of the X-ray source 110, and σ(x, ω, λ1, λ2) denotes a map depending on different projected directions of X-rays.

In a frequency region in which the map σ(x, ω, λ1, λ2) depending on mutually different projected directions of X-rays becomes "0", a back projected image g(x) becomes zero (0) regardless of the projected image f(x), and thereby the back projected image g(x) is lost. A frequency region in which the frequencies are lost to cause noise of the back projected image g(x) in this manner is referred to as the loss frequency region LS.

The map σ(x, ω, λ1, λ2) depending on mutually different projected directions of X-rays may be redefined as shown in the following Equation 8.

$$\sigma(x, \omega, \lambda_1, \lambda_2) = \frac{1}{2}[\text{sgn}(\alpha(x, \lambda_1) \cdot \omega) - \text{sgn}(\alpha(x, \lambda_2) \cdot \omega)] \quad \text{[Equation 8]}$$

where $$\text{sgn}(\alpha(x, \lambda_1) \cdot \omega) = \text{sgn}(\omega_y(y^* - \sqrt{R^2 - x^{*2}}) + \omega_z z^*)$$

$$\text{sgn}(\alpha(x, \lambda_2) \cdot \omega) = \text{sgn}(\omega_y(y^* + \sqrt{R^2 - x^{*2}}) + \omega_z z^*)$$

Here, $\omega_z$ denotes a frequency component with respect to the Z-axis, $\omega_y$ denotes a frequency component with respect to the Y-axis, x' denotes a position of an arbitrary point x on the X-axis, y* denotes a position of an arbitrary point x on the Y-axis, z* denotes a position of an arbitrary point x on the Z-axis, and R denotes a rotation radius of the X-ray source 110.

In addition, α(x, λ1) of Equation 8 denotes a direction vector of the X-ray source 110 and the point x when the rotation angle of the X-ray source 110 is λ1, and α(x, λ2) denotes a direction vector of the X-ray source 110 and the point x when the rotation angle of the X-ray source 110 is λ2. Specifically, the direction vector may be defined by the following Equation 9.

$$\alpha(x, \lambda) = \frac{x - a(\lambda)}{\|x - a(\lambda)\|} \quad \text{[Equation 9]}$$

Here, a(λ) denotes a point on an orbital surface that satisfies the rotation angle λ of the X-ray source 110.

As shown in FIG. 21, in an arbitrary point x1 positioned on the real π lines RL, no phase difference with the X-ray source 110 exists. Accordingly, the direction vector α(x1, λ1) and the direction vector α(x1, λ2) always have different signs from each other. Thus, the map σ(x, ω, λ1, λ2) of Equation 8 depending on different projected directions of X-rays always has a value other than "0". That is, the loss frequency region LS is not present on the real pi lines RL.

However, in an arbitrary point x2 positioned on the virtual pi lines VL, phase differences φ1 and φ2 with the X-ray source 110 exist. By these phase differences φ1 and φ2, a region in which the direction vector α(x2, λ1) and the direction vector α(x2, λ2) have the same sign is present.

That is, due to the phase differences φ1 and φ2 with respect to the X-ray source 110, the loss frequency region LS in which the map σ(x, ω, λ1, λ2) of Equation 8 depending on different projected directions of X-rays has zero (0) is present on the virtual pi lines VL.

Specifically, as shown in FIG. 22, as the frequency component [1] with respect to the Y-axis is changed, the map σ(x, ω, λ1, λ2) depending on different projected directions of X-rays has "1" or "−1" in a first region (NS 1) and a second region (NS 2) in which the signs of the direction vector α(x2, λ1) and the direction vector α(x2, λ2) are different from each other, and therefore it is possible to generate the back projected image g(x).

However, in the loss frequency region LS in which the signs of the direction vector α(x2, λ1) and the direction vector α(x2, λ2) are the same, the map σ(x, ω, λ1, λ2) depending on different projected directions of X-rays has zero (0).

When the map σ(x, ω, λ1, λ2) depending on different projected directions of X-rays becomes "0" in this manner, the back projected image g(x) has "0" regardless of the value of f(x), and therefore a loss of frequencies may occur in the loss frequency region LS.

The loss frequency region LS is determined depending on the direction of the virtual pi lines VL that generates the back projected image g(x). Specifically, the loss frequency region LS is formed in a direction orthogonal to the direction of the virtual pi lines VL used in the generation of the back projected image g(x).

For example, as shown in a column (a) of FIG. 23, when the virtual pi lines VL are parallel to a direction of a Y-axis of an X-Y plane, the loss frequency region LS is formed in a direction orthogonal to the virtual π lines VL, i.e., a direction parallel to the X-axis.

In addition, as shown in a column (b) of FIG. 23, when the virtual pi lines VL are parallel to a direction of an X-axis of the X-Y plane, the loss frequency region LS is formed in a direction orthogonal to the virtual pi lines VL, i.e., a direction parallel to the Y-axis.

In addition, as shown in a column (c) of FIG. 23, when the virtual pi lines VL form an angle 81 with the X-axis of the X-Y plane, the loss frequency region LS is formed in a direction orthogonal to the virtual π lines VL, i.e., at an angle θ2 with respect to the X-axis. In this instance, the angles θ1 and θ2 have a phase difference of 90°.

In contrast, as shown in a column (d) of FIG. 23, when the virtual pi lines VL form an angle θ2 with respect to the X-axis of the X-Y plane, the loss frequency region LS is formed in a direction orthogonal to the virtual pi lines VL, i.e., at an angle θ1 with respect to the X-axis.

In this manner, the formation direction of the loss frequency region LS is determined depending on the direction of the virtual pi lines VL used in the generation of the back projected image g(x), and therefore it is possible to minimize the loss frequency region LS using the plurality of back projected images g(x) in which the virtual pi lines VL are different from one other.

For example, as shown in FIG. 24, when synthesizing a first restored image f1(x) formed using the virtual pi lines VL parallel to the Y-axis of the X-Y plane and a second restored image f2 formed using the virtual pi lines VL parallel to the X-axis of the X-Y plane, a corrected image fa(x) in which the loss frequency region LS is minimized may be obtained. Hereinafter, the image processing unit 501 that minimizes the loss frequency region LS will be described in detail.

Figure 25:
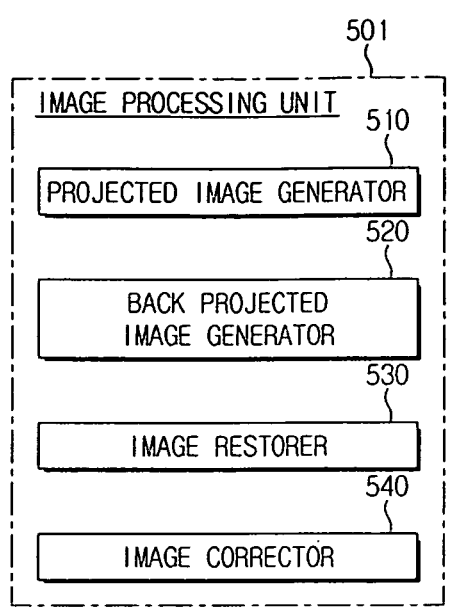
FIG. 25 is a block diagram illustrating an image processing unit of an X-ray imaging apparatus in accordance with another exemplary embodiment.

FIG. 25 is a block diagram illustrating an image processing unit of an X-ray imaging apparatus according to another exemplary embodiment.

As shown in FIG. 25, the image processing unit 501 may include a projected image generator 510, a back projected image generator 520, an image restorer 530, and an image corrector 540.

The projected image generator 510 may receive X-ray signals output from the X-ray detector 120 and generate a projected image with respect to an FOV. The projected image generator 510 is the same as that of the above-described embodiment, and thus detailed description thereof will be omitted.

The back projected image generator 520 generates a back projected image g(x) based on the projected image. In this instance, the back projected image g(x) may be represented in a one-dimensional manner using Equations 1 and 2. The back projected image g(x) generator 520 is the same as that of the above-described embodiment, and thus detailed description thereof will be omitted.

The image restorer 530 may generate restored images for frequency components with respect to the back projected image g(x). For this, the image restorer 530 may include the low frequency component restorer 531, the high frequency component restorer 532, and the image synthesizer 533 which have been described above. The image restorer 530 is the same as that of the above-described embodiment, and thus detailed description thereof will be omitted.

The image corrector 540 minimizes a loss frequency region LS using a plurality of restored images with loss frequency regions which are present in different positions, and thereby corrects noises of the restored images. Hereinafter, an image in which the loss frequency region LS is minimized is defined as a corrected image.

As described above, the position of the loss frequency region may be changed depending on the direction of the virtual pi lines VL used in the generation of the back projected image g(x), and therefore the plurality of restored images used in the generation of the corrected image may be generated from the back projected image generated according to the different pi lines.

In order to minimize the loss frequency region, the image corrector 540 may synthesize a plurality of extraction regions obtained by filtering different positions of the plurality of restored images from the frequency domain, thereby reducing a size of the loss frequency region. In this instance, the filtering position of each restored image may be determined according to the position of the loss frequency region. For example, the filtering direction of each restored image may be determined according to the formation direction of the loss frequency region.

Hereinafter, an exemplary embodiment of generation of the corrected image will be described in detail.

Figure 26:
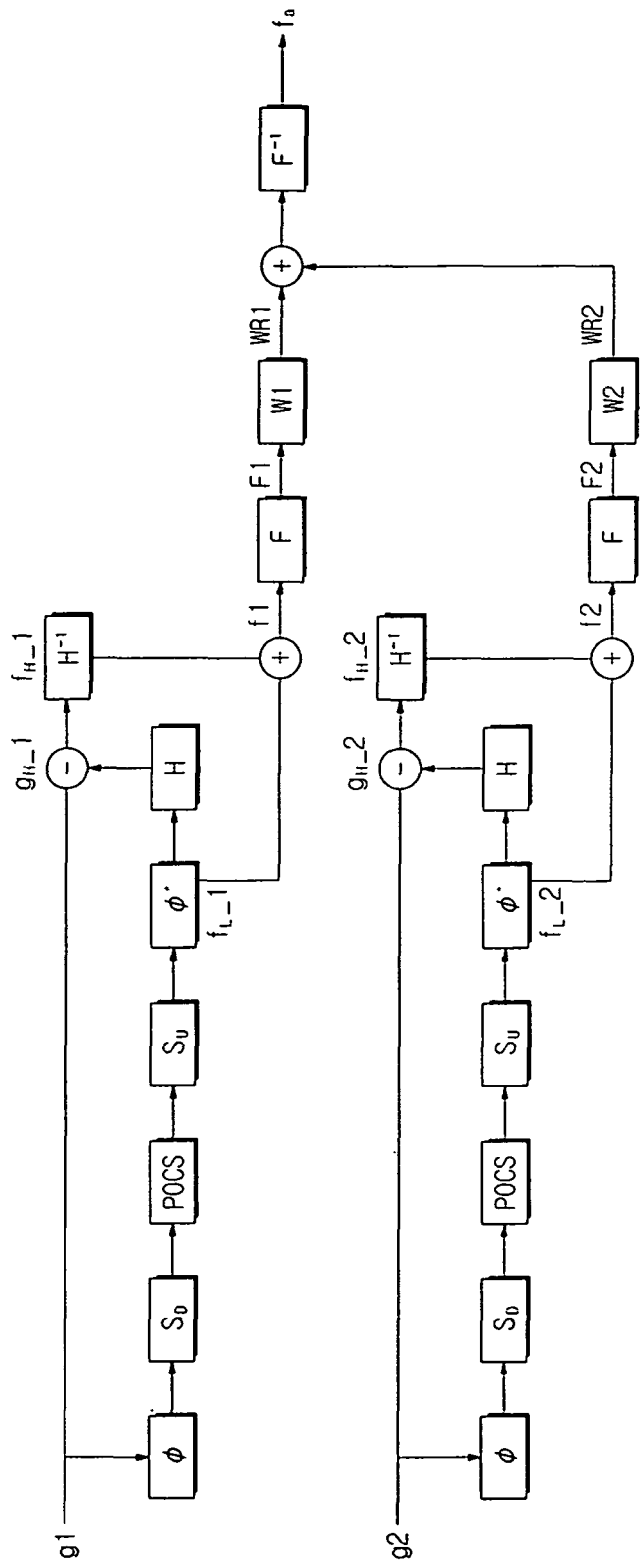
FIG. 26 is a diagram illustrating a process of generating a corrected image using a plurality of restored images in accordance with an exemplary embodiment.
Figure 27:
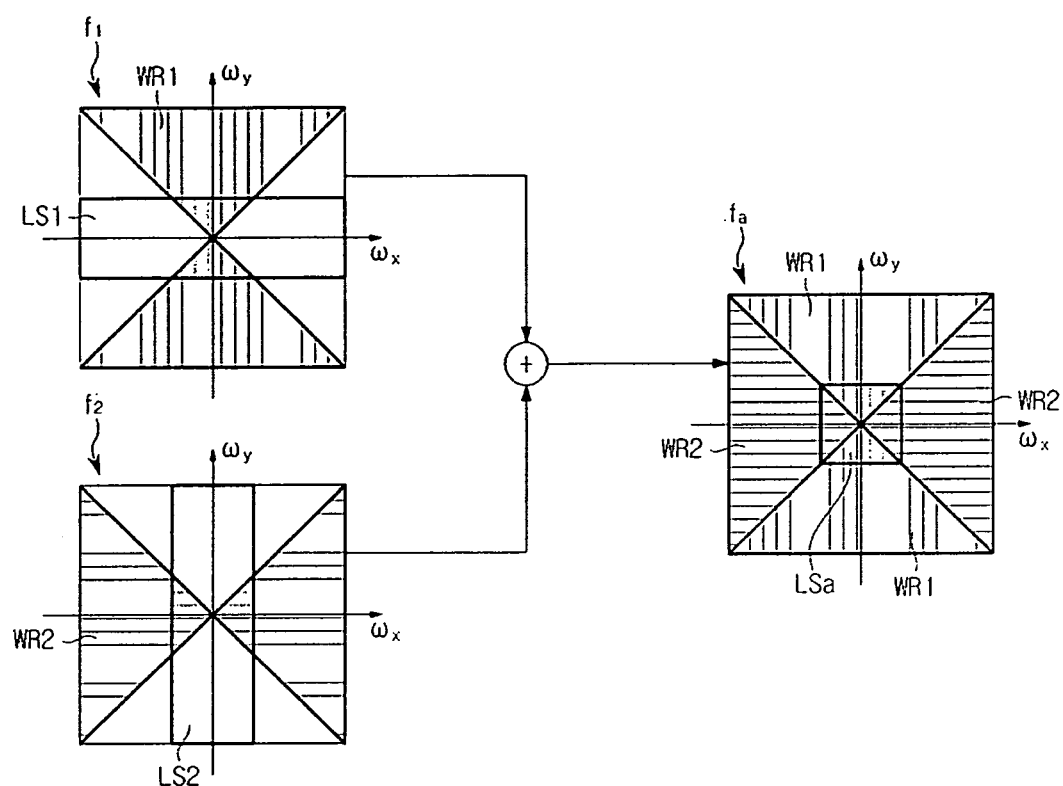
FIG. 27 is a diagram for describing an example of a weight function of FIG. 26.
Figure 28:
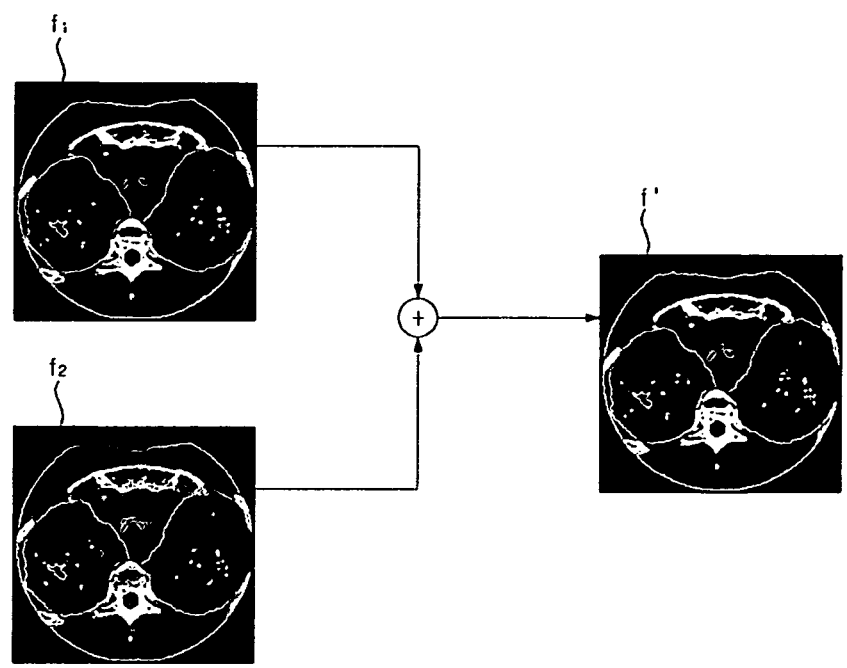
FIG. 28 is a diagram illustrating a process of generating a corrected image of FIG. 26.

FIG. 26 is a diagram illustrating a process of generating a corrected image using a plurality of restored images in accordance with an exemplary embodiment, FIG. 27 is a diagram for describing an example of a weight function of FIG. 26, and FIG. 28 is a diagram illustrating a process of generating a corrected image of FIG. 26.

Referring to FIG. 26, the image corrector 540 may generate a corrected image fa(x) using a plurality of restored images f1 and f2 in which the positions of the loss frequency regions are different from each other.

Here, the plurality of restored images f1 and f2 are positioned on the same virtual orbital surface VT, i.e., the same cross section of the object, so that the virtual pi lines VL are positioned on the same virtual orbital surface VT.

The positions of the loss frequency regions of the restored images f1 and f2 may be determined by the virtual pi lines VL, and therefore the virtual pi lines VL used in the generation of the plurality of back projected images g1 and g2 have different directions on the virtual orbital surface VT.

In this instance, in order to minimize the size of the loss frequency regions overlapped each other, it is preferable that different virtual pi lines VL be orthogonal to each other. For example, the different virtual pi lines may have a relationship in which they are orthogonal to each other as shown in (a) and (b) of FIG. 23, or have a relationship in which they are orthogonal to each other as shown in (c) and (d) of FIG. 23.

Hereinafter, an example in which the virtual pi lines VL of the first back projected image g1 and the virtual pi lines VL of the second back projected image g2 are orthogonal to each other is described, but an angle between the virtual pi lines VL is not limited thereto.

The restored images f1 and f2 may be generated in such a manner that restored images for frequencies are generated based on the frequency components of the back projected images g1 and g2, and the generated restored images for frequencies are synthesized.

Specifically, the image restorer 530 separates low frequency signals and high frequency signals from a first back projected image g1(x) generated according to first pi lines, and generates a low frequency image $f_{L\_1}(x)$ and a high frequency image $f_{H\_1}(x)$ with respect to the separated low frequency signals and the high frequency signals. The image restorer 530 may synthesize the low frequency image $f_{L\_1}(x)$ and the high frequency image $f_{H\_1}(x)$ which have been generated for each of the frequency components, thereby generating a first restored image f1(x).

In addition, in the same manner as that of the first restored image, the image restorer 530 may synthesize a high frequency image $f_{H\_2}(x)$ and a low frequency image $f_{L\_2}(x)$ which have been generated for each frequency in a second back projected image g(x) generated according to second pi lines, thereby generating a second restored image f2(x).

In this instance, the first pi lines and the second pi lines may be orthogonal to each other as described above.

The first restored image f1(x) and the second restored image f2(x) may be sequentially generated. In addition, when the image restorer 530 can be subjected to parallel processing, the first restored image f1(x) and the second restored image f2(x) may be generated in parallel.

In addition, in FIG. 26, an example in which the restored image is generated in the method shown in FIG. 13 has been described, but the method of generating the restored image is not limited thereto. For example, the restored image may be generated in the method shown in FIG. 14 or 15.

The image corrector 540 performs a Fourier transform on each of the plurality of restored images f1(x) and f2(x), thereby transforming the restored images f1(x) and f2(x) to the frequency domain. The restored images transformed into the frequency domain may be defined as image signals F1 and F2.

The image corrector 540 may synthesize a plurality of extracted regions obtained by filtering, in different directions, the restored images transformed to the frequency domain.

Specifically, the image corrector 540 may filter the image signals F1 and F2 by applying predetermined weight functions W1 and W2 to the image signals F1 and F2 transformed to the frequency domain.

Regions which are filtered using the weight functions and output are referred to as selection regions WR1 and WR2. The selection regions WR1 and WR2 which are filtered using the weight functions W1 and W2 may be determined according to the position of the loss frequency region LS that exists in the image signals F1 and F2. That is, the weight functions W1 and W2 may be determined in a direction in which the size of the loss frequency region LS filtered from the image signals F1 and F2 is minimized.

In this instance, a sum of the weight functions W1 and W2 applied to the image signals F1 and F2 may become "1" or greater. That is, a sum of the selection regions WR1 and WR2 which are output by applying the weight functions W1 and W2 thereto may be at least the same as the size of the input image signals F1 and F2. Hereinafter, an exemplary embodiment of the weight function and the selection region will be described in detail with reference to FIG. 27.

Specifically, the image corrector 540 may apply the first weight function W1 to the first image signal F1, thereby extracting the first selection region WR1 from the first image signal F1.

The loss frequency region LS1 in the first image signal F1 may be positioned in the longitudinal direction of the center, and therefore the first weight function W1 may be applied to the first image signal F1 so that the first region WR1 can be extracted in a narrow sandglass shape whose upper and lower portions are wide and whose loss frequency region LS is narrow, thereby minimizing the extraction of the loss frequency region LS.

In addition, the image corrector 540 may extract the second region WR2 from the second image signal F2 by applying the second weight function W2 to the second image signal F2.

The loss frequency region LS2 in the second image signal F2 may be positioned along the height at the center, and therefore the second weight function W2 may be applied to the second image signal F2 so that the second region WR2 can be extracted in a narrow butterfly shape whose right and left sides are wide and whose loss frequency region LS is narrow, thereby minimizing the extraction of the loss frequency region LS.

In this instance, a sum of the first weight function W1 and a second weight function W2 may become "1." That is, a sum of the first region WR1 that is filtered by the first weight function W1 and extracted and the second region WR2 that is filtered and extracted using the second weight function W2 may be the same as the size of the image signals F1 and F2.

The image corrector 540 may synthesize the plurality of regions WR1 and WR2 extracted by the weight functions W1 and W2, thereby generating a single corrected image signal Fa. The corrected image signal Fa may be generated by the plurality of regions WR1 and WR2 extracted by minimizing the loss frequency region LS, and therefore a loss frequency region LSa of the corrected image signal Fa may be minimized as shown in FIG. 27.

The image corrector 540 may perform an inverse Fourier transform on the corrected image signal Fa, thereby acquiring the corrected image fa(x).

In this manner, by minimizing the loss frequency region LS using the plurality of restored images, it is possible to acquire the corrected image whose noise is minimized as shown in FIG. 28.

The series of operations of the corrected image generation method also shown in FIG. 26 may be represented by the following Equation 10.

$$fa(x) = \mathcal{F}^{-1}((W1)\mathcal{F}(f_1(x)) + (W2)\mathcal{F}(f_2(x)))$$ [Equation 10]

Here, $f_a(x)$ denotes the corrected image, $f_1(x)$ denotes a first restored image, $f_2(x)$ denotes a second restored image with the loss frequency region that is orthogonal to that of the first restored image, W1 denotes a first weight function that filters the first restored image so that the loss frequency region is minimized, W2 denotes a second weight function that filters the second restored image in a direction orthogonal to the first weight function, F denotes a Fourier transform, and $F^{-1}$ denotes an inverse Fourier transform.

Meanwhile, in FIG. 26, an example in which the corrected image is generated using two restored images is illustrated, but the larger number of restored images may be used in the generation of the corrected image.

Figure 29:
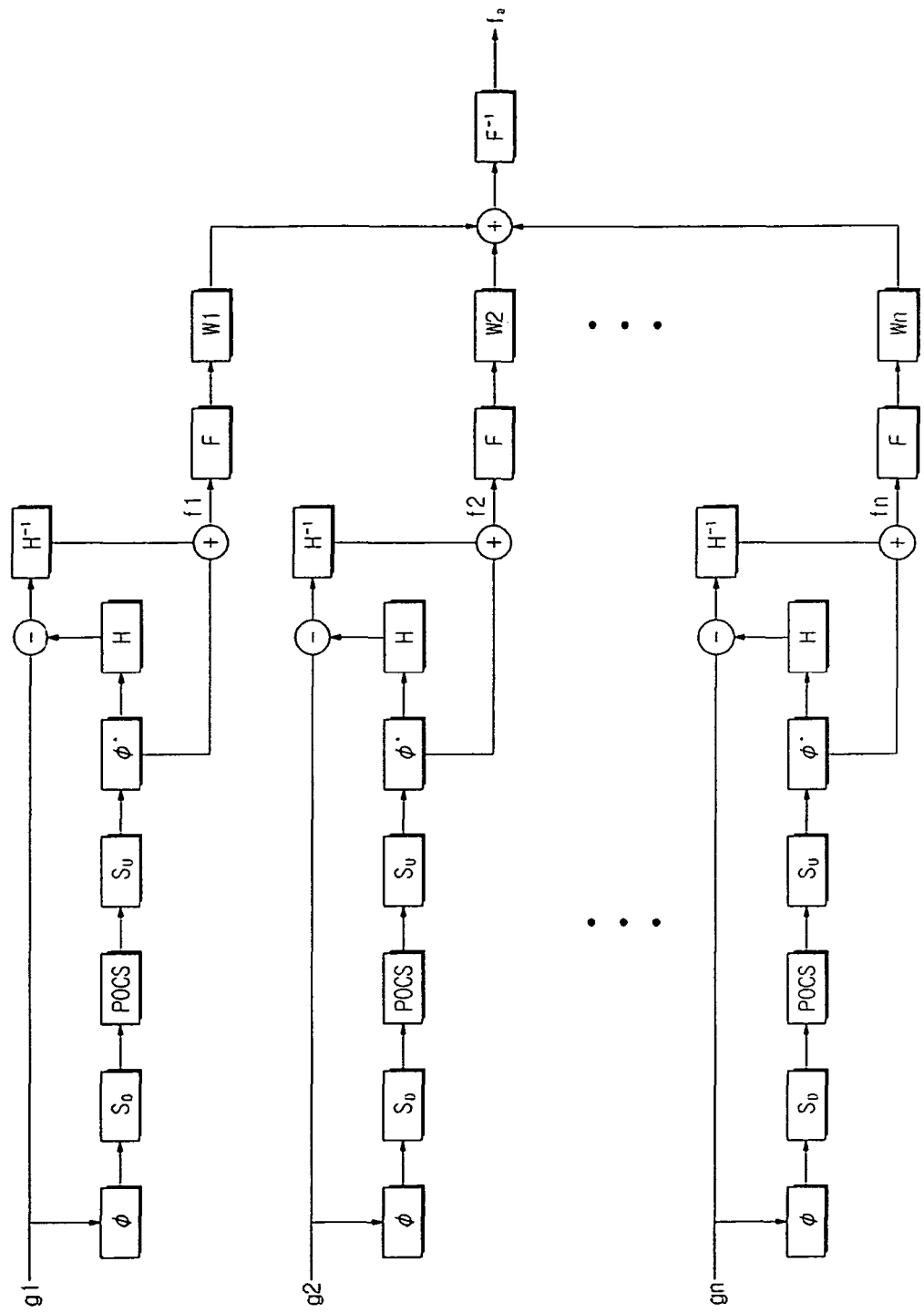
FIG. 29 is a diagram for describing generation of a corrected image using n restored images.
Figure 30:
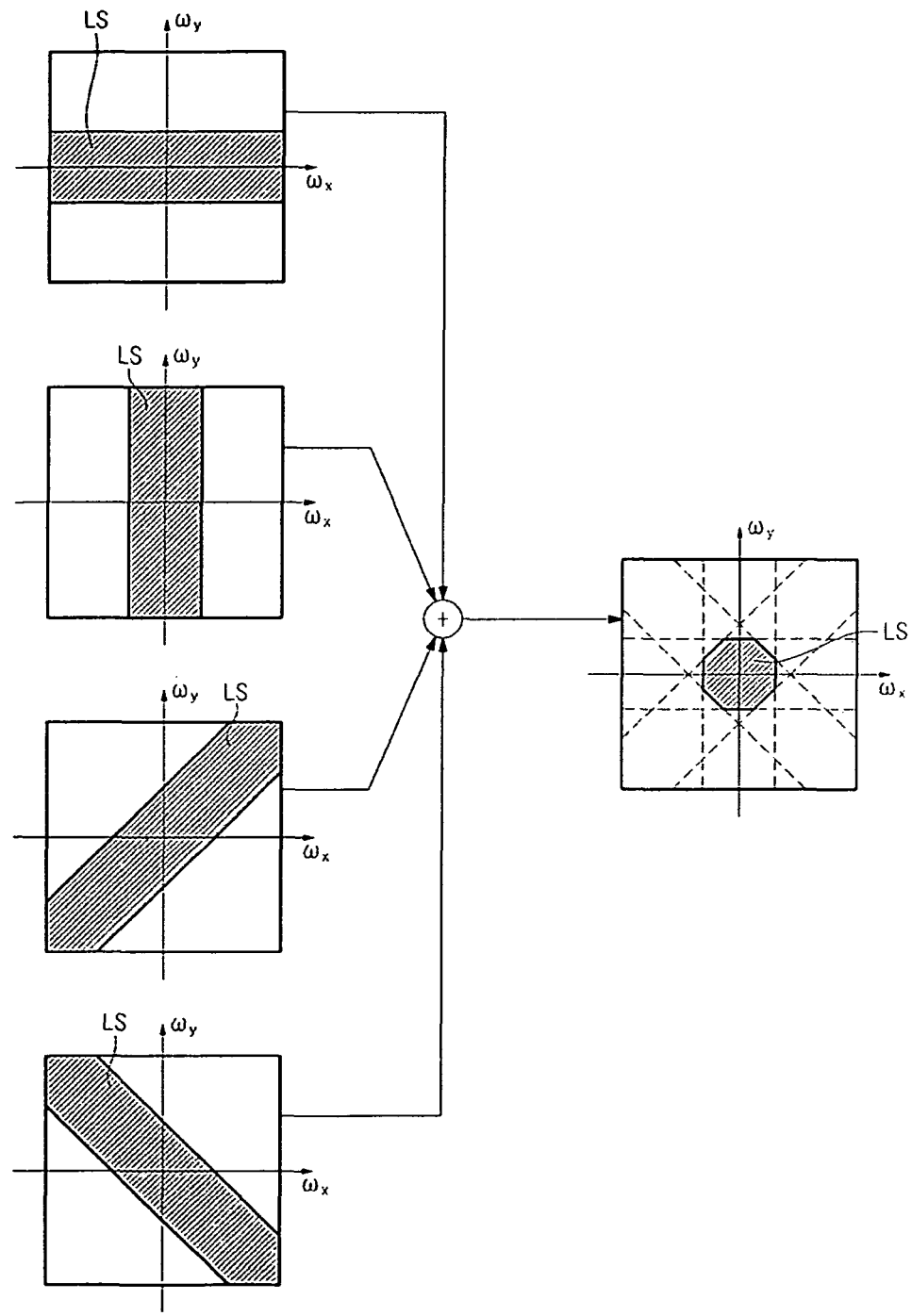
FIG. 30 is a diagram for describing a loss frequency region when different 4 restored images are used.
Figure 31:
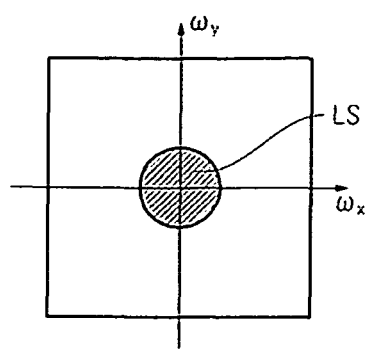
FIG. 31 is a diagram for describing a loss frequency region of a corrected image generated using n restored images.

FIG. 29 is a diagram for describing generation of a corrected image using n restored images, FIG. 30 is a diagram for describing a loss frequency region when using different 4 restored images, and FIG. 31 is a diagram for describing a loss frequency region of a corrected image generated using n restored images.

Referring to FIG. 29, the image corrector 340 may generate a corrected image fa(x) using n restored images f1(x) to fn(x). In this instance, back projected functions g1(x) to gn(x) used in the generation of the n restored images f1(x) to fn(x) all relate to the same virtual orbital surface VT, and pi lines used in the generation of the back projected functions g1(x) to gn(x) are all different from each other.

The image corrector 340 transforms the n restored images f1(x) to fn(x) to the frequency domain by performing a Fourier transform, and generates the corrected image f(a) based on signals acquired by synthesizing selection regions filtered by applying the weight function in the frequency domain.

In this instance, the weight functions W1 to Wn may be determined according to the direction of the loss frequency region that is present in each of the restored images f1(x) to fn(x). That is, the weight functions W1 to Wn may be determined so that the loss frequency region of each selection region that is filtered and output may be minimized.

As shown in FIG. 23, the directions of the pi lines and the loss frequency region are orthogonal to each other, and therefore the weight functions W1 to Wn may be applied so that the selection region is filtered in the direction of the pi lines.

In addition, a sum of the weight functions W1 to Wn which are used in the generation of the corrected image may become "1."

The series of operations of the corrected image generation method shown in FIG. 29 may be represented by the following Equation 11.

$$fa(x) = \mathcal{F}^{-1}\left(\sum_{i=1}^{N} W_i \mathcal{F}(f_i(x))\right) \text{ where } \sum_{i=1}^{n} W_i = 1$$ [Equation 11]

Here, $f_a(x)$ denotes the corrected image, $f_i(x)$ denotes the restored images having different loss frequency regions, $W_i$ denotes a weight function for filtering the restored image, F denotes a Fourier transform, and $F^{-1}$ denotes an inverse Fourier transform.

For example, as shown in FIG. 30, when using four restored images in the generation of the corrected image, the loss frequency region LS is further reduced compared to when two restored images are used in the generation of the corrected image, and therefore noise of the corrected image is further reduced compared to when the two restored images are used in the generation of the corrected image.

In addition, as the number n of restored images used in the generation of the corrected image is increased, the loss frequency region LS converges into a sphere as shown in FIG. 31. That is, the noise removal capacity is improved along with an increase in the number n of the restored images, but the larger number of restored images is required to be processed, and therefore the operation amount of the image processing unit 501 is increased. Thus, the number of restored images used in the generation of the corrected image may be determined according to the performance of the image processing unit 501 and required image quality of the restored images.

Figure 32:
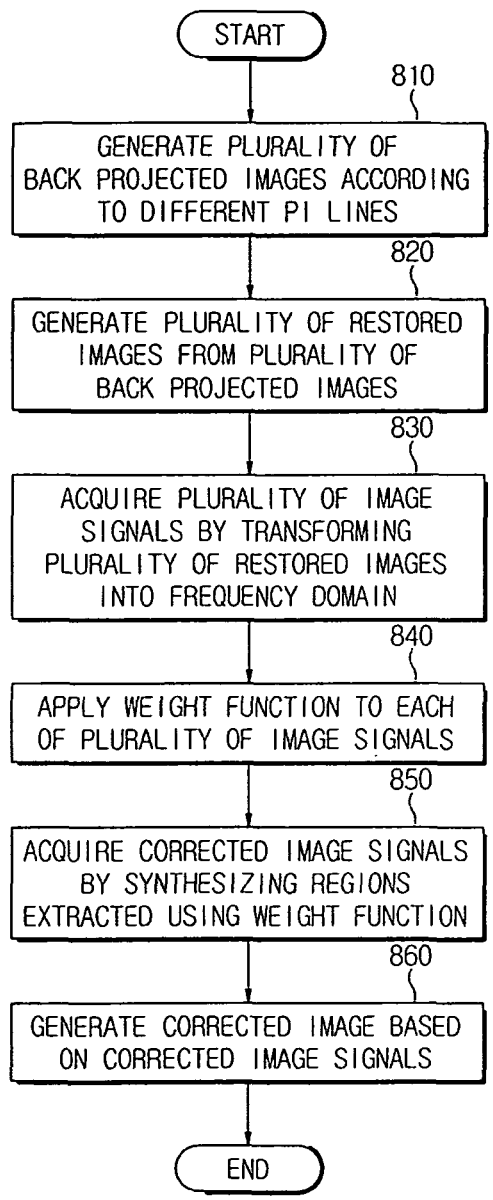
FIG. 32 is a flowchart illustrating a control method for an X-ray imaging apparatus in accordance with another exemplary embodiment.

FIG. 32 is a flowchart illustrating a control method for an X-ray imaging apparatus in accordance with another exemplary embodiment.

Referring to FIG. 32, in operation 810, the X-ray imaging apparatus 2 generates a plurality of back projected images according to mutually different pi lines. That is, the image processing unit 501 may generate the back projected image g(x) according to the different pi lines using Equations 1 and 2. The generation method for the back projected image is the same as that of the above-described exemplary, and thus detailed description thereof will be omitted.

In operation 820, the X-ray imaging apparatus 2 generates a plurality of restored images from a plurality of back projected images. In this instance, directions of virtual lines of the back projected images used in the generation of the restored image are different from each other, and therefore directions of the loss frequency regions which are present in the respective restored images are also different from each other. The restored image generation method is the same as that of the above-described exemplary embodiment, and thus detailed description thereof will be omitted.

In operation 830, the X-ray imaging apparatus 2 transforms the plurality of restored images to the frequency domain, thereby acquiring a plurality of image signals. The image corrector 540 may transform each of the plurality of restored images to the frequency domain by performing a Fourier transform.

In operation 840, the X-ray imaging apparatus 2 applies a weight function to each of a plurality of image signals. The image corrector 540 may minimize the loss frequency region LS by applying the weight function to the image signal transformed to the frequency domain.

The weight function may be applied to the image signal to filter the image signals, thereby partially extracting only a region of the image signals. The region that is filtered by the weight function and extracted may be determined according to a position of the loss frequency region that is present in the image signal, specifically, a direction of the loss frequency region. That is, the weight function may be determined in a direction in which the size of the loss frequency region LS is minimized.

In addition, a sum of the weight functions may be "1" or greater. That is, a sum of the regions extracted by the weight functions may be the same as the size of the input image signal.

In operation 850, the X-ray imaging apparatus 2 synthesizes the regions extracted by the weight functions, thereby acquiring a corrected image signal. Each region extracted from each image signal by the weight functions includes only a minimal loss frequency region, and therefore the loss frequency region of the corrected image signal may be minimized.

In operation 860, the X-ray imaging apparatus 2 generates a corrected image based on the corrected image signal. That is, the image corrector 540 may perform an inverse Fourier transform on the corrected image signal, thereby acquiring the corrected image from the corrected image signal.

According to the X-ray imaging apparatus and the control method for the same according to exemplary embodiments, a restored image may be generated with respect to a whole region of an object or only a partial region thereof. In particular, even when partial information of the inside of the object is not known, or when the FOV includes only a part of the inside of the object, the restored image may be generated, and therefore it is possible to reduce an exposure level of X-rays by reducing a radiation range of X-rays on the object.

In addition, it is possible to reduce a generation time of the restored image by reducing an operation amount for image restoration and complexity of the operation.

Although a few exemplary embodiments have been shown and described, it would be appreciated by those skilled in the art that changes may be made in these exemplary embodiments without departing from the principles and spirit of the exemplary embodiments, the scope of which is defined in the claims and their equivalents.

What is claimed is:

1. An X-ray imaging apparatus comprising:
an X-ray source configured to radiate X-rays onto an object; and
at least one processor configured to:
    generate a back projected image with respect to a projected image of a field of view (FOV),
    acquire a first low frequency component of the back projected image,
    generate a low frequency restored image based on the first low frequency component,
    acquire a high frequency component of the back projected image based on the low frequency restored image,
    generate a high frequency restored image based on the high frequency component,
    generate a restored image with respect to the back projected image by synthesizing the high frequency restored image and the low frequency restored image, and
    generate a corrected image by minimizing a loss frequency region using a plurality of restored images which are different from one another with respect to the loss frequency region.

2. The X-ray imaging apparatus according to claim 1, wherein the at least one processor is further configured to acquire the first low frequency component by applying at least one of low pass filtering (LPF) and down sampling to the back projected image.

3. The X-ray imaging apparatus according to claim 1, wherein the at least one processor is further configured to generate the low frequency restored image by applying a regulation function and a repetitive restoration method to the first low frequency component.

4. The X-ray imaging apparatus according to claim 1, wherein the at least one processor is further configured to generate the low frequency restored image by applying a projection onto convex set (POCS) to the first low frequency component.

5. The X-ray imaging apparatus according to claim 1, wherein the at least one processor is further configured to acquire a second low frequency component of the back projected image by performing a Hilbert transform on the low frequency restored image, and acquire the high frequency component using a difference between the back projected image and the second low frequency component.

6. The X-ray imaging apparatus according to claim 5, wherein the at least one processor is further configured to generate the high frequency restored image using the following Equation:

$$f_H(x) = \frac{H^{-1}\{w(x) \cdot g_H(x)\}}{w(x)} = \frac{-H\{w(x) \cdot g_H(x)\}}{w(x)}$$

where $f_H(x)$ denotes the high frequency restored image, $g_H(x)$ denotes the high frequency component, $w(x)$ denotes a window function corresponding to the second low frequency component, H denotes the Hilbert transform, and $H^{-1}$ denotes an inverse Hilbert transform.

7. The X-ray imaging apparatus according to claim 1, wherein the at least one processor is further configured to generate a corrected image by correcting noise that occurs in the restored image due to a frequency loss.

8. The X-ray imaging apparatus according to claim 7, wherein the at least one processor is further configured to generate the corrected image in which a loss frequency region where the frequencies are lost is minimized using a plurality of restored images which are different from one another with respect to the loss frequency region.

9. The X-ray imaging apparatus according to claim 8, wherein the at least one processor is further configured to generate the corrected image in which the loss frequency region is minimized by synthesizing a plurality of extracted regions obtained by filtering the plurality of restored images in a frequency domain in different directions.

10. The X-ray imaging apparatus according to claim 9, wherein the at least one processor is further configured to determine a direction of the filtering according to a direction of the loss frequency region that is present in the restored image.

11. The X-ray imaging apparatus according to claim 8, wherein the at least one processor is further configured to generate the plurality of restored images based on a plurality of back projected images generated according to different pi lines.

12. A control method for an X-ray imaging apparatus, comprising:

generating a back projected image with respect to a projected image of a field of view (FOV) and obtaining frequency components of the back projected image;
acquiring a first low frequency component of the back projected image;
generating a low frequency restored image based on the first low frequency component;
acquiring a high frequency component of the back projected image based on the low frequency restored image;
generating a high frequency restored image based on the high frequency component; and
generating a restored image with respect to the projected image by synthesizing the high frequency restored image and the low frequency restored image; and
generating a corrected image by minimizing a loss frequency region using a plurality of restored images which are different from one another with respect to the loss frequency region.

13. The control method for the X-ray imaging apparatus according to claim 12, further comprising acquiring the first low frequency component by applying at least one of low pass filtering (LPF) and down sampling to the back projected image.

14. The control method for the X-ray imaging apparatus according to claim 12, further comprising generating the low frequency restored image by applying a regulation function and a repetitive restoration method to the first low frequency component.

15. The control method for the X-ray imaging apparatus according to claim 12, further comprising generating the low frequency restored image by applying a projection onto convex set (POCS) to the first low frequency component.

16. The control method for the X-ray imaging apparatus according to claim 15, further comprising acquiring a second low frequency component of the back projected image by performing a Hilbert transform on the low frequency restored image, and acquiring the high frequency component using a difference between the back projected image and the second low frequency component.

17. The control method for the X-ray imaging apparatus according to claim 12, further comprising generating a corrected image in which a loss frequency region where the frequencies are lost is minimized using a plurality of restored images which are different from one another with respect to the loss frequency region,
wherein the generating of the corrected image includes generating the corrected image in which the loss frequency region is minimized by synthesizing a plurality of extracted regions obtained by filtering the plurality of restored images in a frequency domain in different directions.

* * * * *